US011574141B2

(12) United States Patent
Iwami et al.

(10) Patent No.: US 11,574,141 B2
(45) Date of Patent: Feb. 7, 2023

(54) DRUG RECOGNIZING APPARATUS, DRUG RECOGNIZING METHOD, AND DRUG RECOGNIZING PROGRAM

(71) Applicant: FUJIFILM Toyama Chemical Co., Ltd., Tokyo (JP)

(72) Inventors: Kazuchika Iwami, Ashigarakami-gun (JP); Masanobu Takashima, Ashigarakami-gun (JP)

(73) Assignee: FUJIFILM TOYAMA CHEMICAL CO., LTD., Tokyo (JP)

(*) Notice: Subject to any disclaimer, the term of this patent is extended or adjusted under 35 U.S.C. 154(b) by 814 days.

(21) Appl. No.: 16/547,208

(22) Filed: Aug. 21, 2019

(65) Prior Publication Data
US 2019/0377977 A1    Dec. 12, 2019

Related U.S. Application Data

(63) Continuation of application No. PCT/JP2018/007235, filed on Feb. 27, 2018.

(30) Foreign Application Priority Data

Mar. 23, 2017 (JP) .............................. JP2017-057785
Nov. 22, 2017 (JP) .............................. JP2017-224318

(51) Int. Cl.
*G06K 9/62* (2022.01)
*G06K 9/20* (2006.01)
(Continued)

(52) U.S. Cl.
CPC .............. *G06K 9/6255* (2013.01); *A61J 1/03* (2013.01); *G06V 10/141* (2022.01);
(Continued)

(58) Field of Classification Search
CPC ....... G06K 9/6255; A61J 1/03; A61J 2205/40; A61J 2200/70; A61J 2205/50; G06V 10/141; G06V 2201/03
See application file for complete search history.

(56) References Cited

U.S. PATENT DOCUMENTS 9,349,076 B1    5/2016  Liu et al.
10,565,545 B2*  2/2020  Yonaha .................. G16H 20/13
(Continued)

FOREIGN PATENT DOCUMENTS

CN     103443617 A    12/2013
CN     104582670 A     4/2015
(Continued)

OTHER PUBLICATIONS

Extended European Search Report dated Feb. 27, 2020, for counterpart European Application No. 18770371.5.
(Continued)

*Primary Examiner* — Michael Collins
(74) *Attorney, Agent, or Firm* — Birch, Stewart, Kolasch & Birch, LLP

(57) ABSTRACT

Provided are a drug recognizing apparatus, a drug recognizing method, and a drug recognizing program capable of enhancing robustness of a master image in a case where a drug is recognized. The drug recognizing apparatus includes an illumination unit that illuminates a drug; an imaging unit that images the illuminated drug; a storage unit that stores a master image for each drug type; a drug position acquiring unit that acquires a position of the drug on the basis of a captured image obtained by the imaging unit; a master image generating unit that generates the master image from a drug area in the captured image; an updating determination unit that determines whether to update the master image on the basis of the position of the drug acquired by the drug position acquiring unit; and a registration unit that registers (Continued)

the master image in the storage unit in a case where it is determined that the master image is to be updated.

26 Claims, 21 Drawing Sheets

(51) Int. Cl.
*A61J 1/03* (2006.01)
*G06V 10/141* (2022.01)
(52) U.S. Cl.
CPC ........ *A61J 2200/70* (2013.01); *A61J 2205/40* (2013.01); *A61J 2205/50* (2013.01); *G06V 2201/03* (2022.01)

(56) References Cited

U.S. PATENT DOCUMENTS

| | | | |
|---|---|---|---|
| 2012/0169464 | A1 | 7/2012 | Aok et al. |
| 2012/0243797 | A1 | 9/2012 | Di Venuto Dayer et al. |
| 2013/0058550 | A1 | 3/2013 | Tanmmoto et al. |
| 2013/0342676 | A1* | 12/2013 | Amano .................. G07F 9/026 348/86 |
| 2015/0170373 | A1 | 6/2015 | Yonaha et al. |
| 2015/0178674 | A1* | 6/2015 | Yonaha .................. G16H 70/40 705/2 |
| 2016/0005160 | A1* | 1/2016 | Ito .......................... G16H 10/60 348/86 |
| 2016/0210524 | A1* | 7/2016 | Hasegawa ............... G06V 10/44 |
| 2017/0264867 | A1 | 9/2017 | Amano et al. |
| 2021/0019886 | A1* | 1/2021 | Iwami .................. G06T 7/0014 |

FOREIGN PATENT DOCUMENTS

| | | |
|---|---|---|
| CN | 104717952 A | 6/2015 |
| CN | 106415251 A | 2/2017 |
| EP | 2 924 647 A1 | 9/2015 |
| EP | 2 959 881 A1 | 12/2015 |
| EP | 3 675 030 A1 | 7/2020 |
| JP | 9-16681 A | 1/1997 |
| JP | 2004-167158 A | 6/2004 |
| JP | 2005-249615 A | 9/2005 |
| JP | 2005-258680 A | 9/2005 |
| JP | 2014-67342 A | 4/2014 |
| JP | 2014-120156 A | 6/2014 |
| JP | 2015-68765 A | 4/2015 |
| WO | WO 2011/030441 A | 3/2011 |
| WO | WO 2015/152225 A1 | 10/2015 |

OTHER PUBLICATIONS

International Preliminary Report on Patentability (Form PCT/IPEA/409) for International Application No. PCT/JP2018/007235, dated Jul. 30, 2018, with English translation.
International Search Report (Form PCT/ISA/210) for International Application No. PCT/JP2018/007235, dated Apr. 17, 2018, with English translation.
Chinese Office Action and Search Report, dated Mar. 3, 2021, for corresponding Chinese Application No. 201880017385.9, with English translations.
European Communication pursuant to Article 94(3) EPC for corresponding European Application No. 18770371.5, dated Nov. 23, 2021.

* cited by examiner

FIG. 13

| | | 22 | |
|---|---|---|---|
| FIRST DRUG PACKAGE | (A) 0.85 | (B) 0.80 | (C) 0.70 |
| SECOND DRUG PACKAGE | (A) 0.85 | (B) 0.85 | (C) 0.90 |
| THIRD DRUG PACKAGE ⋮ | | (B) 0.80 | (C) 0.90 |

FIG. 22

| CAPTURED IMAGE | | FIRST TABLET | | SECOND TABLET | | THIRD TABLET | |
|---|---|---|---|---|---|---|---|
| | | FRONT SURFACE | REAR SURFACE | FRONT SURFACE | REAR SURFACE | FRONT SURFACE | REAR SURFACE |
| | | Ⓑ | ◯ | Ⓐ | ◯ | ⑫ | ◯ |
| MASTER IMAGE OF CANDIDATE DRUG (ASCENDING ORDER IN COINCIDENCE) | FIRST HIGHEST COINCIDENCE | DRUG ID: BBBBB COINCIDENCE: 0.99 | | DRUG ID: AAAAA COINCIDENCE: 0.99 | | DRUG ID: 111222 COINCIDENCE: 0.99 | |
| | | Ⓑ | ◯ | Ⓐ | ◯ | ⑫ | ◯ |
| | SECOND HIGHEST COINCIDENCE | DRUG ID: RRRRR COINCIDENCE: 0.75 | | DRUG ID: ΛΛΛΛΛ COINCIDENCE: 0.80 | | DRUG ID: 111333 COINCIDENCE: 0.70 | |
| | | Ⓡ | ◯ | Ⓥ | ◯ | ⑬ | ◯ |
| | THIRD HIGHEST COINCIDENCE | DRUG ID: DDDDD COINCIDENCE: 0.70 | | DRUG ID: VVVVV COINCIDENCE: 0.75 | | DRUG ID: 222222 COINCIDENCE: 0.45 | |
| | | Ⓓ | ◯ | Ⓥ | ◯ | ② | ◯ |

[ SUBSEQUENTLY DIFFERENTIATE ]    [ END ]    [ TO MENU ]

FIG. 23

| ATTRIBUTE INFORMATION | MASTER IMAGE (FRONT) | MASTER IMAGE (REAR) |
|---|---|---|
| DRUG CODE: XXX-XXXX<br>GENERAL NAME: XXXX<br>ORIGINAL PRODUCT NAME: YYYYY<br>GENERIC PRODUCT NAME: ZZZZZ<br>DRUG TYPE: TABLET<br>SHAPE: CIRCLE<br>DIMENSION: DIAMETER 10mm<br>COLOR: WHITE<br>ENGRAVED MARK: A | Ⓐ | ◯ |

OK

DRUG RECOGNIZING APPARATUS, DRUG RECOGNIZING METHOD, AND DRUG RECOGNIZING PROGRAM

CROSS-REFERENCE TO RELATED APPLICATIONS

The present application is a Continuation of PCT International Application No. PCT/JP2018/007235 filed on Feb. 27, 2018 claiming priorities under 35 U.S.C § 119(a) to Japanese Patent Application No. 2017-057785 filed on Mar. 23, 2017 and Japanese Patent Application No. 2017-224318 filed on Nov. 22, 2017. Each of the above applications is hereby expressly incorporated by reference, in their entirety, into the present application.

BACKGROUND OF THE INVENTION

1. Field of the Invention

The present invention relates to a drug recognizing apparatus, a drug recognizing method, and a drug recognizing program capable of enhancing robustness of a master image in a case where a drug is recognized.

2. Description of the Related Art

A variety of apparatuses that recognize a drug type have been proposed or provided. For example, a technique for illuminating a drug, imaging the illuminated drug, and collating a drug area in an image obtained by the imaging, with a master image that is registered, in advance for each drug type to recognize a drug type has been used.

JP2005-249615A discloses a technique in which, in a wrong type mixing inspection for works that are continuously provided in a production line, in order to prevent a change in recognition accuracy due to external factors such as a change in illumination and a difference between coating states of works, image data of a work that is first provided is registered as a mater image (reference image data), image data of each of plural works that are subsequently provided is compared with the above-mentioned master image, and then, in a case where it is determined that they are the same type, the master image is constantly updated.

Further, JP1997-016681A (JP-H09-016681A) discloses a technique in which a drug information database is retrieved using measurement value characteristics (color tones, sizes, shapes, and the like) of drugs as inquiry retrieval items, and completely matching or approximating product names are displayed on a screen.

In addition, WO2015/152225A discloses a technique in which an image of an illuminated drug is captured and matching between the captured drug image and a template image of each drug stored in a database is performed to perform drug differentiation.

SUMMARY OF THE INVENTION

Even though the technique disclosed in JP2005-249615A is applied to recognition of drugs and the master image is constantly updated in a case where drugs in a drug package are the same type of drugs as those in the master image, it is difficult to enhance robustness of the master image. The reason is that positions of the drugs in the drug package are different from each other for each drug package, in a case where the drugs are imaged at a position with a low recognition, recognition accuracy of the drug is lowered.

JP1997-016681A (JP-H09-016681A) does not disclose collation with a master image and enhancement of robustness of the master image. Further, WO2015/152225A discloses template matching, but does not disclose enhancement of robustness of a master image.

An object of the present invention is to provide a drug recognizing apparatus, a drug recognizing method, and a drug recognizing program capable of enhancing robustness of a master image in a case where a drug is recognized.

In order to achieve the above-mentioned object, according to an aspect of the present invention, there is provided a drug recognizing apparatus comprising: an illumination unit that illuminates a drug; an imaging unit that images the drug illuminated by the illumination unit; a storage unit that stores a master image showing the drug for each drug type; a drug position acquiring unit that acquires a position of the drug on the basis of a captured image obtained by the imaging unit; an updating determination unit that determines whether to update the master image on the basis of the position of the drug acquired by the drug position acquiring unit; a master image generating unit that generates the master image from a drug area in the captured image obtained by the imaging unit; and a registration unit that registers the master image generated by the master image generating unit in the storage unit in a case where the updating determination unit determines that the master image is to be updated.

According to this aspect of the present invention, since the position of the drug is acquired on the basis of the captured image obtained by the imaging unit and it is determined whether to update the master image on the basis of the position of the drug for each drug type, it is possible to update the master image so that a recognition rate of the drug becomes high even in a case where the position of the drug is changed for each drug package. That is, it is possible to enhance robustness of the master image in a case where the drug is recognized.

According to another aspect of the present invention, in the drug recognizing apparatus according to the above aspect of the present invention, the registration unit stores drug position information indicating the position of the drug in association with the master image in the storage unit, and the updating determination unit determines whether to update the master image on the basis of the position of the drug imaged by the imaging unit and the drug position information associated with the master image.

According to still another aspect of the present invention, in the drug recognizing apparatus according to the above aspect of the present invention, the updating determination unit determines that the master image is to be updated in a case where cognitive power for the drug at the position of the drug imaged by the imaging unit is higher than that at the position of the drug in the master image indicated by the drug position information associated with the master image.

According to still another aspect of the present invention, in the drug recognizing apparatus according to the above aspect of the present invention, in a case where a type of drug of which the master image is not registered is imaged by the imaging unit, the registration unit registers the drug area in the captured image obtained by the imaging unit as the master image in the storage unit.

According to still another aspect of the present invention, in the drug recognizing apparatus according to the above aspect of the present invention, the updating determination unit determines whether to update the master image on the basis of a distance between a reference position at which cognitive power for the drug in an imaging range of the imaging unit satisfies a criterion and the position of the drug.

According to still another aspect of the present invention, the drug recognizing apparatus according to the above aspect of the present invention further comprises: a reference position setting unit that calculates in advance the position at which the cognitive power for the drug in the imaging range of the imaging unit satisfies the criterion, and sets the calculated position as the reference position.

According to still another aspect of the present invention, in the drug recognizing apparatus according to the above aspect of the present invention, the reference position is a position at which the cognitive power for the drug in the imaging range is the highest or a representative position in an area at which the cognitive power for the drug is the highest.

According to still another aspect of the present invention, in the drug recognizing apparatus according to the above aspect of the present invention, the cognitive power is cognitive power for an engraved mark on a front surface of the drug, and is determined in accordance with an incident angle at which illumination light of the illumination unit is incident to the mark on the front surface of the drug.

According to still another aspect of the present invention, in the drug recognizing apparatus according to the above aspect of the present invention, the illumination unit illuminates the drug in a plurality of illumination directions surrounding the drug, the imaging unit faces at least one face of a packaging member that wraps the drug, the reference position is a central position in the imaging range, and the updating determination unit determines whether to update the master image on the basis of a distance between the central position in the imaging range and the position of the drug.

According to still another aspect of the present invention, in the drug recognizing apparatus according to the above aspect of the present invention, the illumination unit is configured to include a plurality of light sources, and the plurality of light sources and an optical axis of the imaging unit are disposed at equal intervals.

According to still another aspect of the present invention, in the drug recognizing apparatus according to the above aspect of the present invention, the illumination unit illuminates the drug in four or more directions.

According to still another aspect of the present invention, in the drug recognizing apparatus according to the above aspect of the present invention, the updating determination unit determines whether to update the master image on the basis of intervals of a plurality of the drugs in a case where the plurality of drugs are included in one drug package.

According to still another aspect of the present invention, in the drug recognizing apparatus according to the above aspect of the present invention, the illumination unit is configured to include a plurality of light sources, the drug recognizing apparatus further comprises: an illumination controller that sequentially switches an illumination direction of the drug by switching the light source that illuminates the drug among the plurality of light sources; and an imaging controller that causes the imaging unit to image the drug whenever the illumination direction is switched, and the master image generating unit composes the plurality of captured images corresponding to the plurality of illumination directions, obtained by the imaging unit, to generate the master image.

According to still another aspect of the present invention, in the drug recognizing apparatus according to the above aspect of the present invention, the imaging unit is configured to include a first camera that images the drug in a first direction and a second camera that images the drug in a second direction different from the first direction.

According to still another aspect of the present invention, in the drug recognizing apparatus according to the above aspect of the present invention, the drug is packaged.

According to still another aspect of the present invention, in the drug recognizing apparatus according to the above aspect of the present invention, a plurality of drug packages in which the drug is packaged are continuous, and in a case where the same kind of plural drugs are imaged from one drug package, or in a case where the same kind of plural drugs are imaged over the plurality of drug packages, the master image generating unit generates the master image using a plurality of drug areas in which the same kind of plural drugs are imaged. Here, in a case where only the same kind of one drug is imaged from one drug package, a configuration in which the master image is generated from one drug area may be used. Further, in a case where the same kind of plural drugs are not imaged over the plurality of drug packages, the master image may be generated from one drug area.

According to still another aspect of the present invention, in the drug recognizing apparatus according to the above aspect of the present invention, in a case where the same kind of plural drugs are imaged from one drug package, or in a case where the same kind of plural drugs are imaged over the plurality of drug packages, the master image generating unit generates the master image using an average or a weighted average using the plurality of drug areas.

According to still another aspect of the present invention, the drug recognizing apparatus according to the above aspect of the present invention further comprises: a display unit; and a display controller that causes the display unit to display the drug area in the captured image.

According to still another aspect of the present invention, the drug recognizing apparatus according to the above aspect of the present invention further comprises: a correlation value calculation unit that calculates a correlation value between the master image and the drug area in the captured image, and the display controller causes the display unit to display the correlation value.

According to still another aspect of the present invention, in the drug recognizing apparatus according to the above aspect of the present invention, the display controller causes the display unit to display a history of the updating of the master image.

According to still another aspect of the present invention, in the drug recognizing apparatus according to the above aspect of the present invention, the display controller causes the display unit to display the position of the drug and the updating of the master image in association.

According to still another aspect of the present invention, the drug recognizing apparatus according to the above aspect of the present invention further comprises: a drug determination unit that collates a master image that is finally registered among the master images registered in the storage unit with the captured image to determine what the drug indicated by the captured image is; and a determination result output unit that outputs a determination result. According to this aspect of the present invention, the captured image is collated with the master image that is finally registered (that is, the master image with enhanced robustness according to the above described aspect). Therefore, it is possible to reliably determine what the drug indicated by the captured image is. The drug recognizing apparatus according to this aspect can be applied to drug differentiation and drug inspection support.

According to still another aspect of the present invention, in the drug recognizing apparatus according to the above aspect of the present invention, the drug determination unit selects a candidate of the drug indicated by the captured image on the basis of the collation result between the captured image and the master image, and the determination result output unit outputs information indicating the selected candidate. According to this aspect of the present invention, it is possible to confirm the candidate of the drug indicated by the captured image on the basis of the output information.

According to still another aspect of the present invention, in the drug recognizing apparatus according to the above aspect of the present invention further comprises: an associated information input unit for inputting associated information relating to the drug indicated by the captured image, and the drug determination unit performs the determination with reference to the associated information. According to this aspect of the present invention, it is possible to input information to be used in drug collation as associated information, and to accurately perform the determination with reference to the associated information.

According to still another aspect of the present invention, in the drug recognizing apparatus according to the above aspect of the present invention, the associated information is information on a drug included in prescription data, and the drug determination unit acquires the master image for the drug included in the prescription data from the storage unit, collates the captured image with the acquired master image, and determines whether the drug indicated by the captured image is identical to the drug indicated by the acquired master image. According to this aspect of the present invention, by inputting the information on the drug included in the prescription data as the associated information, it is possible to accurately determine whether the drug indicated by the captured image and the drug indicated by the master image are equal to each other.

According to still another aspect of the present invention, there is provided a drug recognizing method that uses an illumination unit that illuminates a drug, an imaging unit that images the drug illuminated by the illumination unit, and a storage unit that stores a master image showing the drug for each drug type, the method comprising: a step of acquiring a position of the drug on the basis of a captured image obtained by the imaging unit; a step of determining whether to update the master image on the basis of the acquired position of the drug; and a step of registering a drug area in the captured image as the, master image in the storage unit in a case where it is determined that the master image is to be updated.

According to still another aspect of the present invention, there is provided a drug recognizing program for causing a computer to execute the drug recognizing method according to the above aspect of the present invention. According to still another aspect of the present invention, there is provided a non-transitory computer-readable recording medium on which the drug recognizing program according to the above aspect of the present invention is recorded.

According to the drug recognizing apparatus, the drug recognizing method, and the drug recognizing program according to the present invention, it is possible to enhance robustness, of a master image in a case where a drug is recognized.

BRIEF DESCRIPTION OF THE DRAWINGS

FIG. 13 is a diagram showing a display example of a drug recognition result.

FIG. 22 is a diagram showing an example of a result obtained by applying the drug recognizing method and apparatus according to the present invention to the drug differentiation.

FIG. 23 is a diagram showing another example of the result obtained by applying the drug recognizing method and apparatus according to the present invention to the drug.

DESCRIPTION OF THE PREFERRED EMBODIMENTS

Hereinafter, embodiments of a drug recognizing apparatus, a drug recognizing method, and a drug recognizing program according to the present invention will be described with reference to the accompanying drawings.

Figure 1:
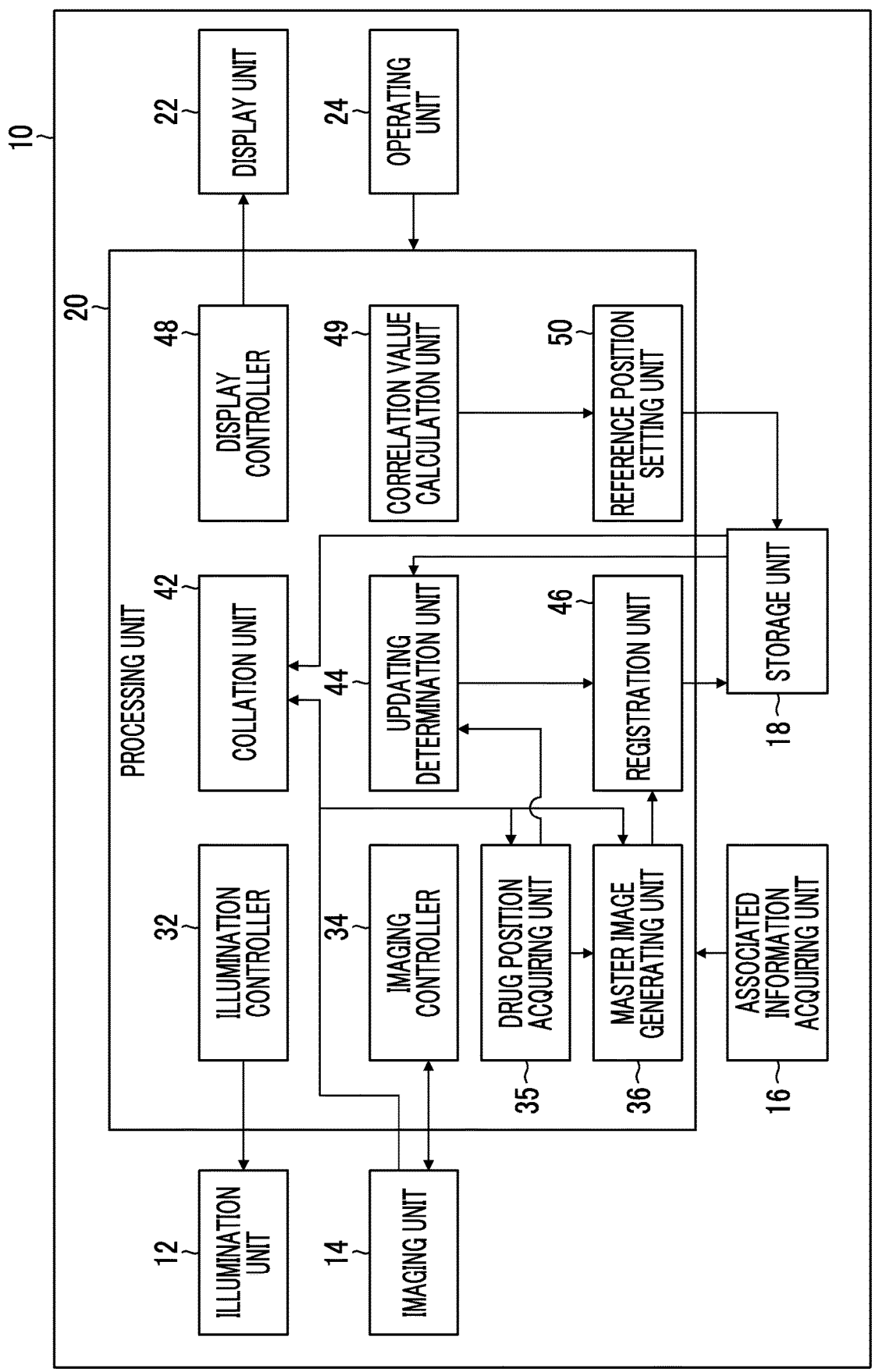
FIG. 1 is a diagram showing a configuration example of a drug recognizing apparatus according to an embodiment of the present invention.

FIG. 1 is a diagram showing a configuration example of the drug recognizing apparatus according to an embodiment of the present invention.

A drug recognizing apparatus 10 of this example includes an illumination unit 12 that illuminates drugs, an imaging unit 14 that images the drugs illuminated by the illumination unit 12, an associated information acquiring unit 16 that acquires associated information relating to drugs that are recognition targets, such as prescription data indicating prescription of drugs for a user, a storage unit 18 (non-temporary recording medium) that stores a program (including the drug recognizing program according to the present invention) and information necessary for execution of the program, a processing unit 20 that performs a variety of processes in accordance with the program stored in the storage unit 18, a display unit 22 on which an image may be displayed, and an operating unit 24 that receives an operation from a user. Hereinafter, a case where drugs are packaged will be described, but the present invention may be applied to a case where drugs are not packaged (which will be described later).

The "packaging" of drugs includes "one packaging". The "one packaging" means that prescribed drugs are dividedly packaged for one-time dose. Depending on prescription details, there are a case where different kinds of plural drugs are packaged in one packaging member, a case where the same kind of plural drugs are packaged in one packaging member, and a case where only one drug is packaged in one packaging member. Types of drugs to be packaged may include, for example, tablets or capsules, but are not particularly limited. Further, the packaging member may be made of paper or plastics, for example, but is not limited thereto. Further, in this specification, the "divided packaging" is not limited to a case where drugs are dividedly packaged for one-time dose, and may include any case where drugs are packaged according to packaging members.

The illumination unit 12 includes light sources. A specific example of the illumination unit 12 will be described later.

The imaging unit 14 includes cameras. A specific example of the imaging unit 14 will be described later.

The associated information acquiring unit 16 optically reads out characters on a prescription, for example, to acquire associated information of prescription data or the like. The prescription data may include, for example, identification information of drugs written on a prescription, names, quantities, directions for use, doses, or the like, but is not limited thereto. The associated information acquiring unit 16 may read out barcodes (or 2-dimensional codes) given to the prescription to acquire the prescription data. Further, prescription data input by a doctor and/or a pharmacist through a computer apparatus may be acquired through communication. The "prescription data" may be information written on the prescription, or may be information set or changed by the doctor and/or the pharmacist on the basis of the information written on the prescription. For example, in a case where a name of an original drug is written on a prescription, information obtained by changing the original drug to a generic drug, or in a case where only a general drug name is written on a prescription, information obtained by selecting the original drug or the generic drug, for example, may also be included in the "prescription data". In a case where the drug recognizing apparatus 10 is used in drug inspection support, drug differentiation, or the like (which will be described later), features of drugs that are visually recognized (for example, drug types such as tablets or capsules, shapes, colors, or the like), or information such as drug names, quantities, or directions for use written on a pocketbook such as a so-called "drug history handbook" may be input by the associated information acquiring unit 16 (associated information input unit) in accordance with a user's operation.

The storage unit 18 is configured by a temporary storage device and a non-temporary storage device (non-temporary recording medium). The storage unit 18 in this example stores a master image (may be referred to as a "drug master image") indicating a drug for each drug type. It is preferable that the master image is stored in association with attribute information indicating an attribute of each drug (for example, information on a drug code, a name, a drug type, a shape, a dimension, or the like, see an example of FIG. 23).

The processing unit 20 is configured by a central processing unit (CPU), for example. The processing unit 20 of this example has a function for updating the master images stored in the storage unit 18. In a case where a specific condition (which will be described later) is satisfied, the processing unit 20 of this example performs a master updating process of updating the master images stored in the storage unit 18 using captured images obtained by the imaging unit 14.

The processing unit 20 of this example is configured to include an illumination controller 32 that controls illumination of the illumination unit 12, an imaging controller 34 that controls imaging of the imaging unit 14, a drug position acquiring unit 35 that acquires a position of a drug on the basis of a captured image obtained by the imaging unit 14, a master image generating unit 36 that generates a master image from a drug area in the captured image obtained by the imaging unit 14, a collation unit 42 that collates the drug area of the captured image obtained by imaging the drug by the imaging unit 14 with the master image stored in the storage unit 18, an updating determination unit 44 that determines whether to update the master image on the basis of the position of the drug obtained by the drug position acquiring unit 35, a registration unit 46 that registers the master image generated by the master image generating unit 36 in the storage unit 18 in a case where it is determined that the master image is to be updated by the updating determination unit 44, and a display controller 48 that controls display of the display unit 22. A correlation value calculation unit 49 that calculates a correlation value between the master image and the drug area in the captured image or a correlation value between the drug areas, and a reference position setting unit 50 that sets a reference position may be included.

Drug Package

Figure 2:
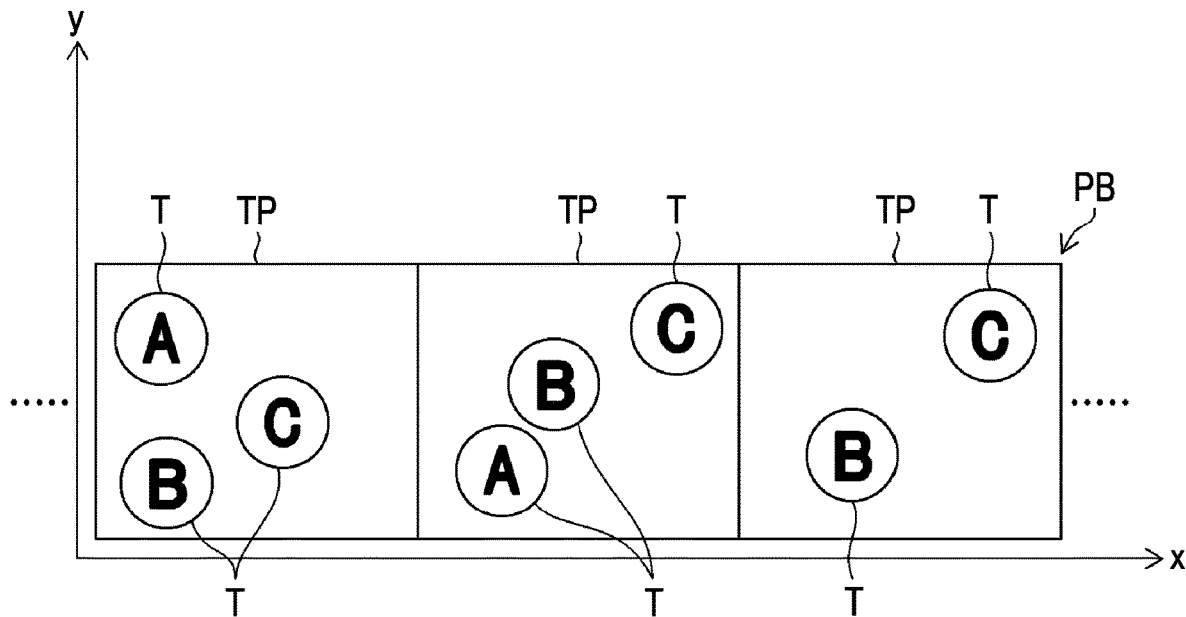
FIG. 2 is a diagram showing an example in which a plurality of cartridges are continued.

FIG. 2 shows a package bandage PB in which a plurality of drug packages TP in which drugs T are packaged are continued. An x-axis represents an axis along a length direction of the package bandage PB, and a y-axis represents an axis along a width direction of the package bandage PB. The package bandage PB of this example may be transported along the x-axis. Types of the drugs T are shown in the drugs T of this example through engrave-marking (or printing). Hereinafter, for ease of description, it is assumed that "A", "B", or "C" are engraved in the respective drugs T, but marking details (or printing details) are not particularly limited.

It is preferable that a packaging member of the drug package TP is transparent on both faces (including semi-transparent, which is similarly applied hereinafter). Printing or matt finishing may be performed on one face of the packaging member of the drug package TP.

The continuous drug packages TP may be transported in the unit of each size of one drug package TP in the x-axis direction. For each drug package TP, the position of the drug package TP may be detected.

The present invention is not limited to a case where the drug package TP is transported. The present invention may be applied to a case where the drug package TP is merely placed on a placing table or the like. Further, the present invention may be a case where the drugs T are not packaged. For example, respective drugs included in the drugs T may be directly placed on the placing table, or may be placed on the placing table in a state of being contained in a container such as a schale.

Illumination Unit and Imaging Unit

Disposition of the light sources that form the illumination unit 12 and the cameras that form the imaging unit 14 will be described hereinafter.

Figure 3:
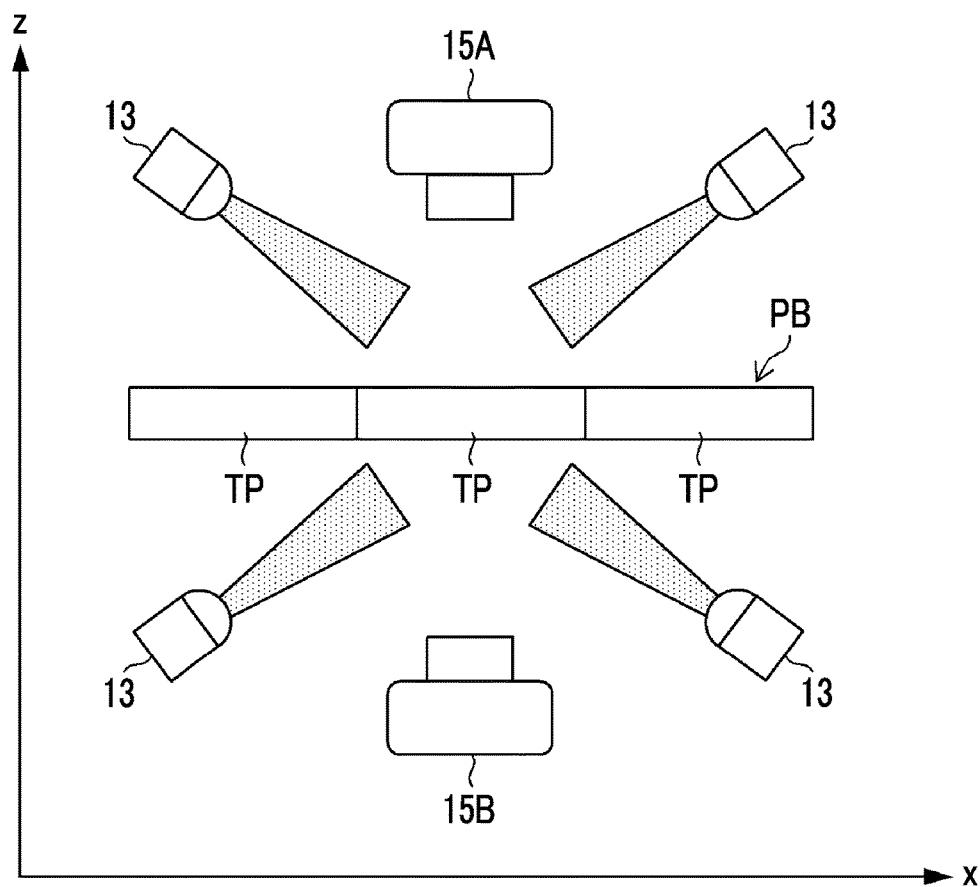
FIG. 3 is a side view showing a disposition example of light sources of an illumination unit and cameras of an imaging unit.
Figure 4:
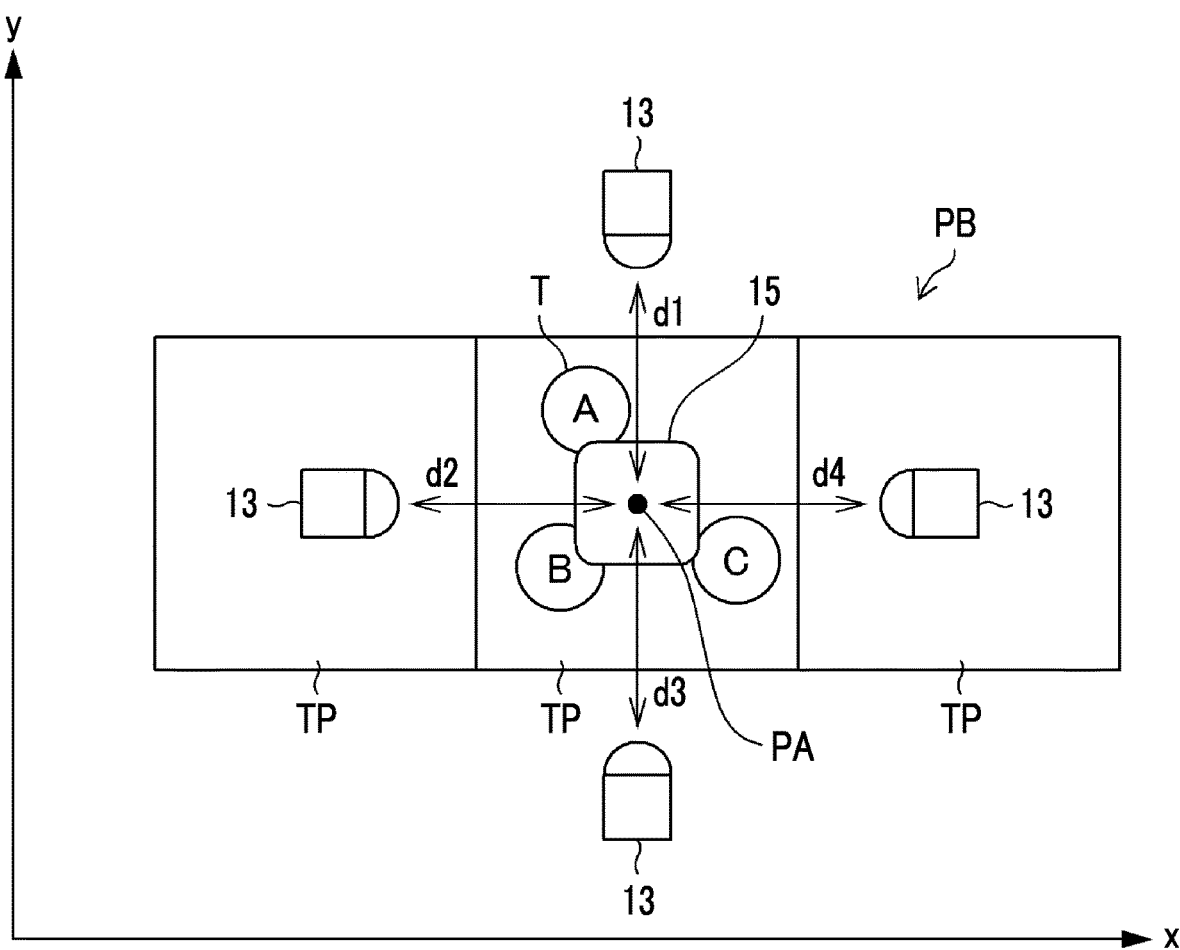
FIG. 4 is a plan view showing a disposition example of light sources of an illumination part and a camera of an imaging part.

FIGS. 3 and 4 are diagrams showing a disposition example of light sources 13 of the illumination unit 12 and cameras 15 (15A and 15B) of the imaging unit 14. FIG. 3 is a side view seen from a side face of the package bandage PB, and FIG. 4 is a plan view when one face of the package bandage PB is seen from the top or bottom. An x-axis represents an axis along the length direction of the package bandage PB, a y-axis represents an axis along the width direction of the cartridge PB, and a z-axis represents an axis perpendicular to one face (an upper face or a lower face) of the cartridge PB.

The illumination unit 12 is configured to include the plurality of light sources 13, and as shown in FIG. 4, illuminates the drugs T in a plurality of illumination directions surrounding the drugs T. The illumination unit 12 of this example illuminates one face (an upper face or a lower face) of the drugs T in four directions. The drugs T may be illuminated in four or more directions.

The imaging unit 14 faces at least one side of a transparent packaging member that wraps the drugs T to image the drugs T.

As shown in FIG. 3, the imaging unit 14 is configured to include the camera 15A (a first camera) that faces the upper face of the package bandage PB (one face of the packaging member that packages the drugs T) and the camera 15B (a second camera) that faces the lower face (the other face of the packaging member that packages the drugs T) of the package bandage PB. That is, the camera 15A images the drugs T in a first direction (direction from the upside of the package bandage PB to the downside thereof), and the camera 15B images the drugs T in a second direction (direction from the downside of the package bandage PB to the upside thereof). In FIG. 4, intervals d1, d2, d3, and d4 between each of the plurality of light sources 13 and imaging optical axes PA of the cameras 15 (15A and 15B) are equal to each other. That is, distances between the plurality of light sources 13 and the imaging optical axes PA are equal intervals (d1=d2=d3=d4).

Generation and Updating Determination of Master Image

The master image generating unit 36 extracts drug areas from captured images obtained by the cameras 15 of the imaging unit 14 to generate master images. For example, the drug areas are recognized by detecting edges of images of the drugs T from the captured images, and the drug areas are extracted by cutting out the drug areas from the captured images. In the extraction of the drug areas, two images obtained by imaging the drugs T in both upper and lower directions may be used. An image in which a drug background is changed may be used. A mask is generated using transmission images (in which drug areas are black) formed by transmitted light that passes through the packaging member of the drug package TP, and the master images may be generated using the mask.

In a case where a type of drug T of which a master image is not registered is imaged by the cameras 15 of the imaging unit 14, the registration unit 46 sets a drug area in a newly captured image obtained by the cameras 15 as the master image, and registers the result in the storage unit 18. Further, in a case where it is determined that the master image is to be updated using the updating determination unit 44, the master image in the storage unit 18 is updated.

The updating determination will be described. The drug position acquiring unit 35 acquires drug positions in an imaging range of the imaging unit 14, on the basis of the captured images obtained by the imaging unit 14. The drug position acquiring unit 35 of this example acquires positions of images of the drugs T in the captured images through image analysis. That is, since the positions of the drugs T in the imaging range of a real space and the positions of the images of the drug T in the captured images correspond to each other, the positions of the images of the drugs T in the captured images may be used as the positions of the drugs in the imaging range.

Further, the acquisition of "the positions of the drugs" is not limited to a case where absolute positions of the drugs in the imaging range (or the captured images) is acquired, in this specification, and includes a case where distances (hereinafter, may be referred to as "relative positions") to a reference position where cognitive power for the drugs satisfies a criterion in the imaging range (or the captured images) are acquired. That is, the updating determination unit 44 may determine whether to update the master images on the basis of the relative positions.

Further, the "cognitive power" for the drugs is cognitive power for recognizing the types of the drugs on the basis of the captured images in this specification. Generally, the cognitive power is changed in accordance with the drug positions in the imaging range. The "cognitive power" may be represented by a recognition probability (recognition rate), or may be represented by an evaluation value that is calculated in advance. For example, the evaluation value that represents the cognitive power using correlation values between the drug images may be shown as described later.

As a specific example, in a case where an engraved mark indicating the type of the drug is formed on the front surface of the drug, the "cognitive power" is cognitive power for the mark of the front surface of the drug. Generally, the cognitive power for the mark of the front surface of the drug is determined in accordance with angles (incident angles) at which illumination light of the illumination unit 12 is incident to the mark of the front surface of the drug. Further, in a case where a printed mark indicating the type of the drug is formed on the front surface of the drug, the "cognitive power" is cognitive power for the printed mark of the front surface of the drug. Generally, the cognitive power for the printing of the front surface of the drug is determined in accordance with angles (imaging angles) of the optical axes (imaging optical axes) of the imaging unit 14 with respect to the printing of the front surface of the drug.

Figure 5:
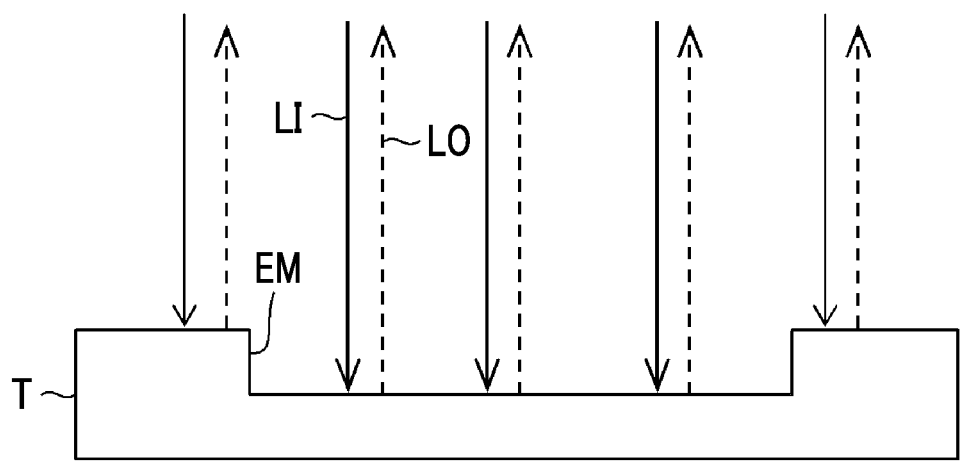
FIG. 5 is a diagram showing a condition on which detection of drug marking becomes difficult.
Figure 6:
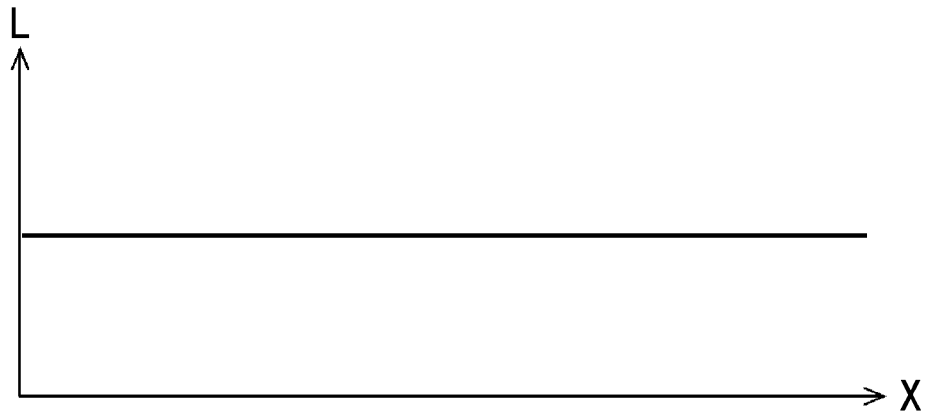
FIG. 6 is a diagram showing a brightness distribution in the case shown in FIG. 5.

In a case where the light sources 13 and the cameras 15 are disposed as shown in FIG. 4, it is preferable that a master image is an image of a drug placed in a central area of the imaging range ("visual field range") of the cameras 15. This is because in the case of the disposition example shown in FIG. 4, the image of the drug imaged in the central area of the imaging range has a high robustness, but an image of a drug imaged at an edge (that is, in the vicinity of the light source 13) of the imaging range has a low robustness. For example, a tablet (which is one type of drug) is formed in a 3-dimensional (3D) shape, and as the tablet gets close to the light source 13, an incident angle of illumination light becomes small with respect to an engraved mark of the tablet, which leads to difficulty in detection of the engraved mark. For ease of understanding, as shown in FIG. 5, it is assumed that incident light beams LI indicated by solid lines and reflecting light beams LO indicated by dashed lines are parallel to a side face of a concave portion of an engraved mark EM of the tablet T. Then, as shown in FIG. 6, it can be understood that a brightness profile L indicating a brightness distribution of a captured image has a flat shape and the engraved mark EM cannot be detected.

Thus, the updating determination unit 44 determines whether to update the master images on the basis of the distances between the reference position at which the cognitive power for the drugs in the imaging range of the imaging unit 14 satisfies the criterion and the positions of the drugs. Here, the determination based on the "distances between the reference position and the positions of the drugs" may be performed using the reference position, the positions of the drugs and the distances in the captured image corresponding to the reference position, the positions of the drugs and the distances in the real space.

For example, the reference position is a position at which the cognitive power for the drugs in the imaging range is the highest, or a representative position of an area in which the cognitive power for the drugs in the imaging range is the highest.

In a case where the light sources 13 and the cameras 15 are disposed as shown in FIG. 4, a central position in the imaging range (which is the position of the imaging optical axis PA in the imaging range in the real space, and in the captured image, is the center of the image) may be set as the reference position. In this case, the updating determination unit 44 determines whether to update the master images on the basis of the distances between the central position in the imaging range and the positions of the drugs. Accordingly, it is possible to enhance the accuracy of drug recognition using the master images. That is, it is possible to enhance the robustness of the master images. A position in the vicinity of the central position in the imaging range may be set as the reference position.

Figure 7:
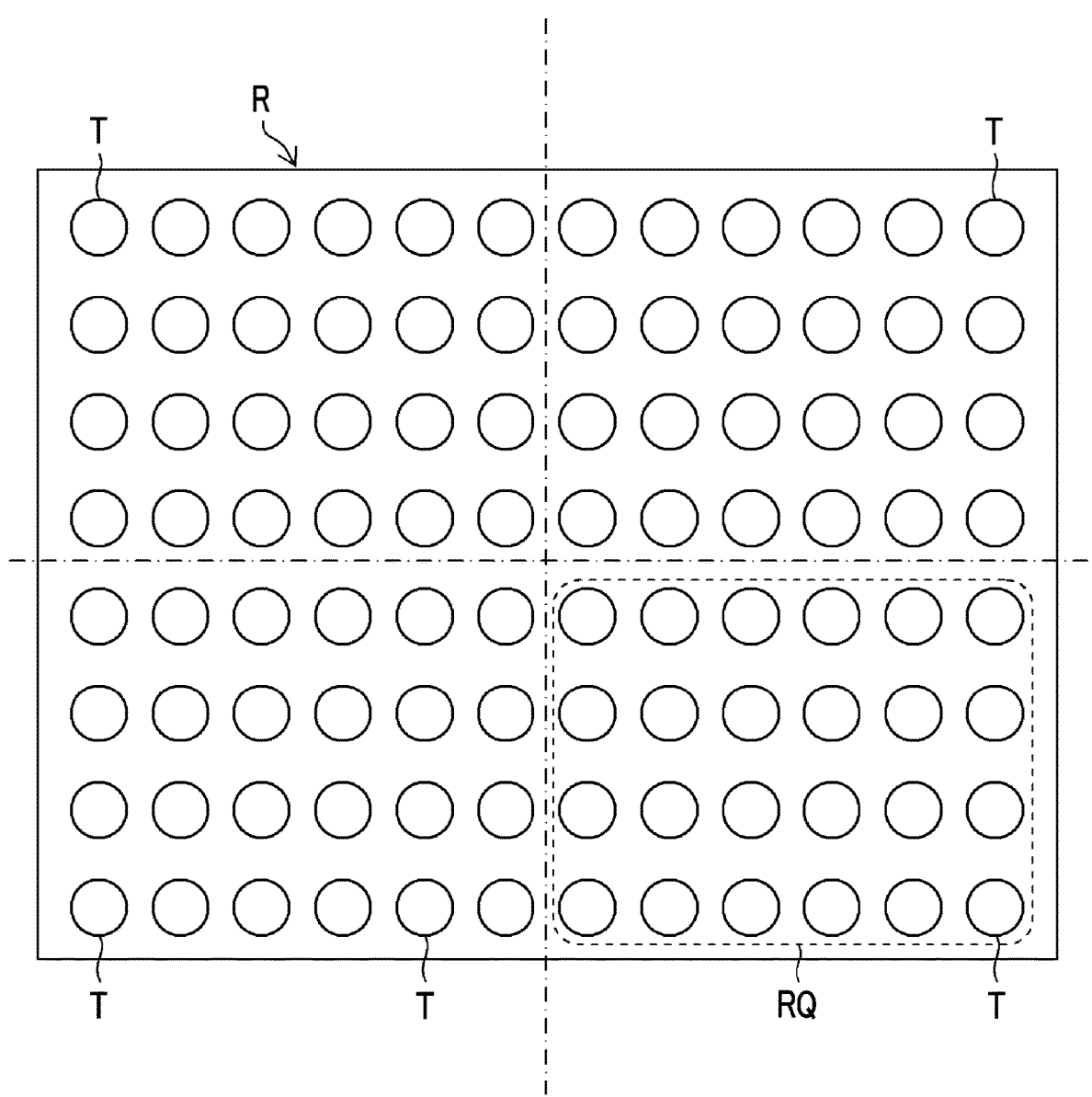
FIG. 7 is a diagram showing drugs that are two-dimensionally arranged for reference position setting.
Figure 8:
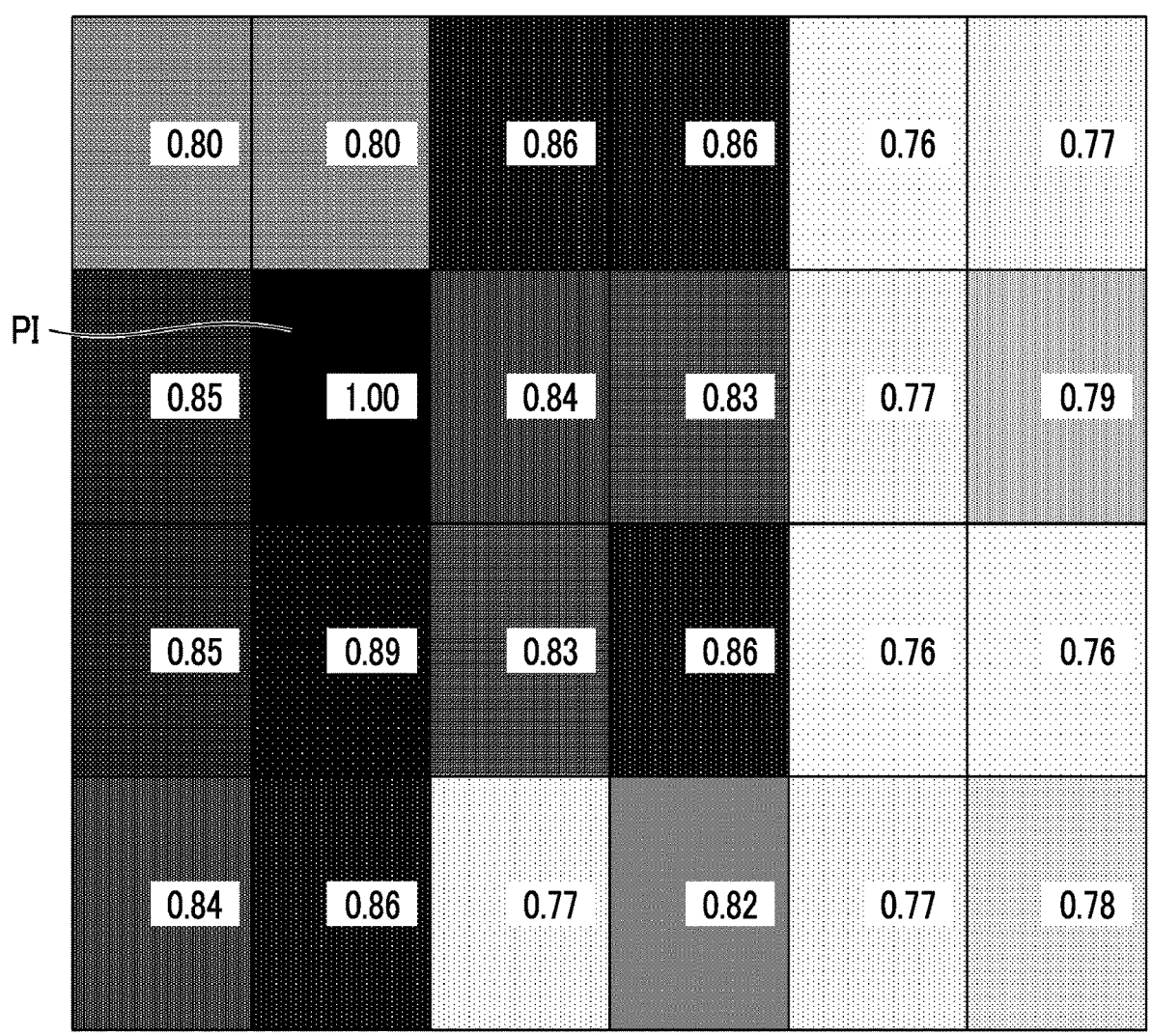
FIG. 8 is a diagram used for description of calculation of correlation values for the reference position setting.

Further, a method for calculating in advance a position at which the cognitive power for the drugs in the imaging range is high (a position at which the cognitive power for the drugs satisfies the criterion), and setting the calculated position as the reference position using the reference position setting unit 50 may be used. For example, as shown in FIG. 7, a method for arranging a plurality of drugs T at equal intervals in a 2-dimensional form in an imaging range R, imaging the plurality of drugs T that are arranged in the 2-dimensional form by the cameras 15, calculating a correlation value of a drug image (an image of a drug area) at a position of each drug T with respect to the other drugs T by the correlation value calculation unit 49, and obtaining an area in which the cognitive power in the imaging range R is the highest on the basis of the correlation values. For ease of understanding, correlation values of drug images between drug positions in a quarter area RQ having a size of one fourth of the imaging range R shown in FIG. 7 are shown in FIG. 8. In FIG. 8, a self-correlation value (a correlation value between a drug image of an attention position PI and the drug image of the attention position PI) is "1.00". Further, in FIG. 8, a correlation value between the drug image of the attention position PI and a drug image of another position is smaller than "1.00". The calculated correlation values are indicated by numerical values and colors (in FIG. 8, for ease of illustration, gradation is used). The calculation of the correlation values may be performed by setting respective positions of the plurality of drugs T that are arranged in the two-dimensional form in the imaging range R as attention positions, and setting an attention position at which distribution of the correlation values becomes most preferable in the entirety of the imaging range R (or in a range necessary for drug recognition) as the reference position. For example, a total sum of correlation values with respect to the other positions is calculated for each attention position, and an attention position at which the total sum of the correlation values becomes maximum is set as the reference position. That is, a representative position of an area in which the cognitive power in the imaging range R is the highest may be set as the reference position. Basically, it is preferable to image the drugs in a case where the drugs are placed at the central portion of the imaging range R, but since the positions of the packaged drugs vary in respective cartridges, the drugs may be unintentionally imaged at an end portion of the imaging range R. That is, in a case where the master images are unconditionally updated, the accuracy of drug recognition using the master images may be lowered. In this example, since an attention position at which the cognitive power for the drugs in the imaging range R satisfies the criterion is calculated in advance to set the attention position as a reference position by the reference position setting unit 50 and it is determined whether to update the master images on the basis of distances between the reference position and actual drug positions imaged in drug recognition, it is possible to enhance the accuracy of the drug recognition using the master images by updating the master images. That is, it is possible to enhance the robustness of the master images.

The registration unit 46 of this example stores drug position information indicating positions of drugs in an imaging range (or distances between the reference position and the positions of the drugs) in the storage unit 18 in association with the master images. Further, the updating determination unit 44 determines whether to update the master images on the basis of the positions of the drugs imaged by the imaging unit 14 (or the distances between the reference position and the positions of the drugs), and the drug position information associated with the master images.

The updating determination unit 44 of this example determines that the master image is to be updated in a case where the position of the drug imaged by the imaging unit 14 is closer to the reference position than the position of the drug of the master image indicated by the drug position information associated with the master image.

Figure 9:
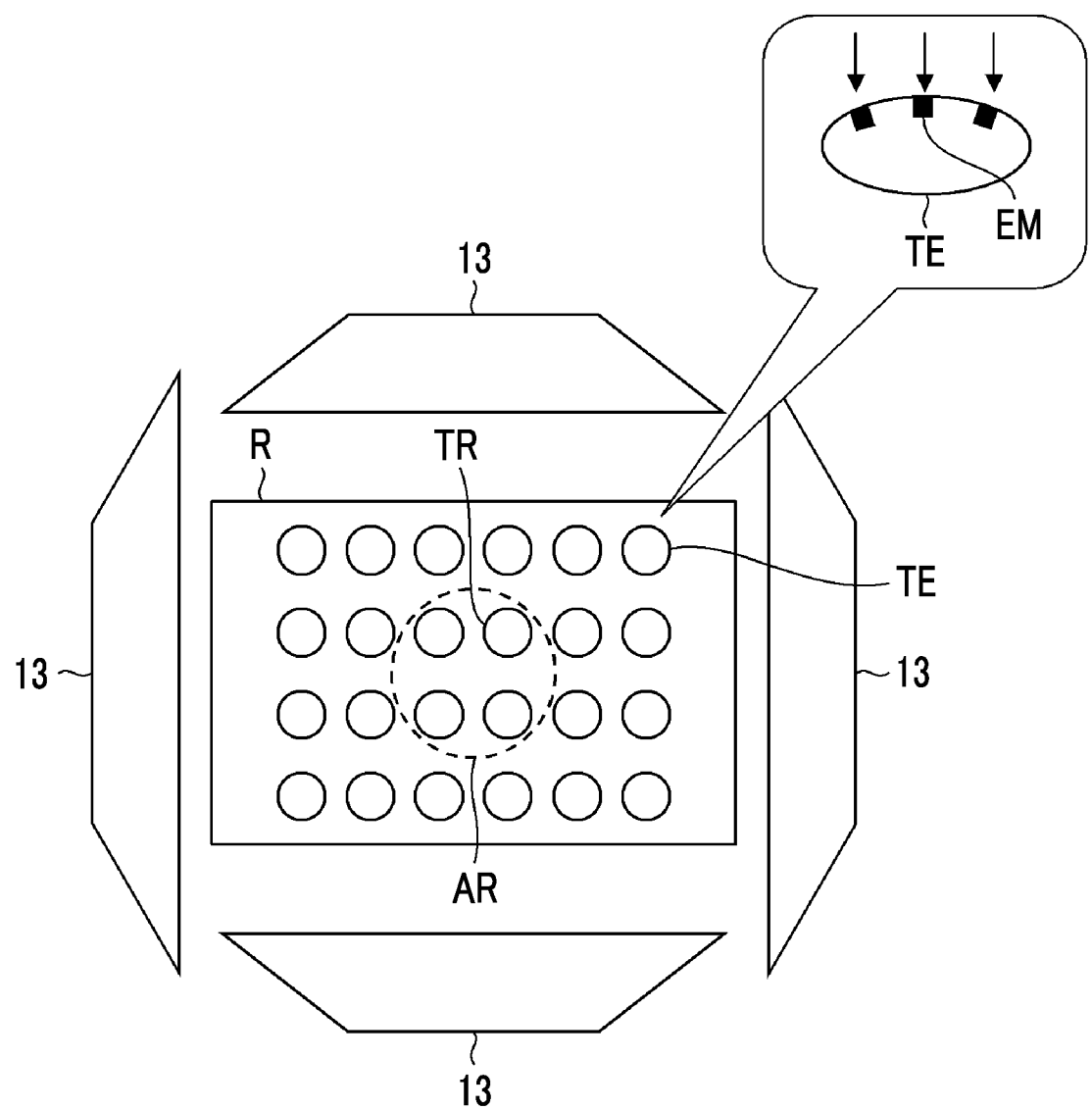
FIG. 9 is a diagram used for description of preferable updating of a master image.

The master images registered in the storage unit 18 through updating based on the above-described criterion are sequentially updated to better master images. That is, as shown in FIG. 9, the updating is performed until an image of a drug TR in an area AR at which the robustness of the master image is high in the imaging range R becomes the master image. In a case where an image of a drug (in the figure, a drug TE) at an end portion where the robustness of the master image is low in the imaging range R is registered as the master, cognitive power of an engraved mark EM is low. However, in this example, since a master image is converged to a better master image and the image of the drug TR in the area AR based on the criterion is registered as the master image, it is possible to enhance the cognitive power of the engraved mark EM. In the disposition of the plurality of light sources 13 and the cameras 15 shown in FIG. 4 (in which the distances between the plurality of light sources 13 and the imaging optical axis PA are equal intervals), drug positions of the master images gradually comes close to the position of the imaging optical axis PA that is the central position in the imaging range R.

Collating

Figure 10:
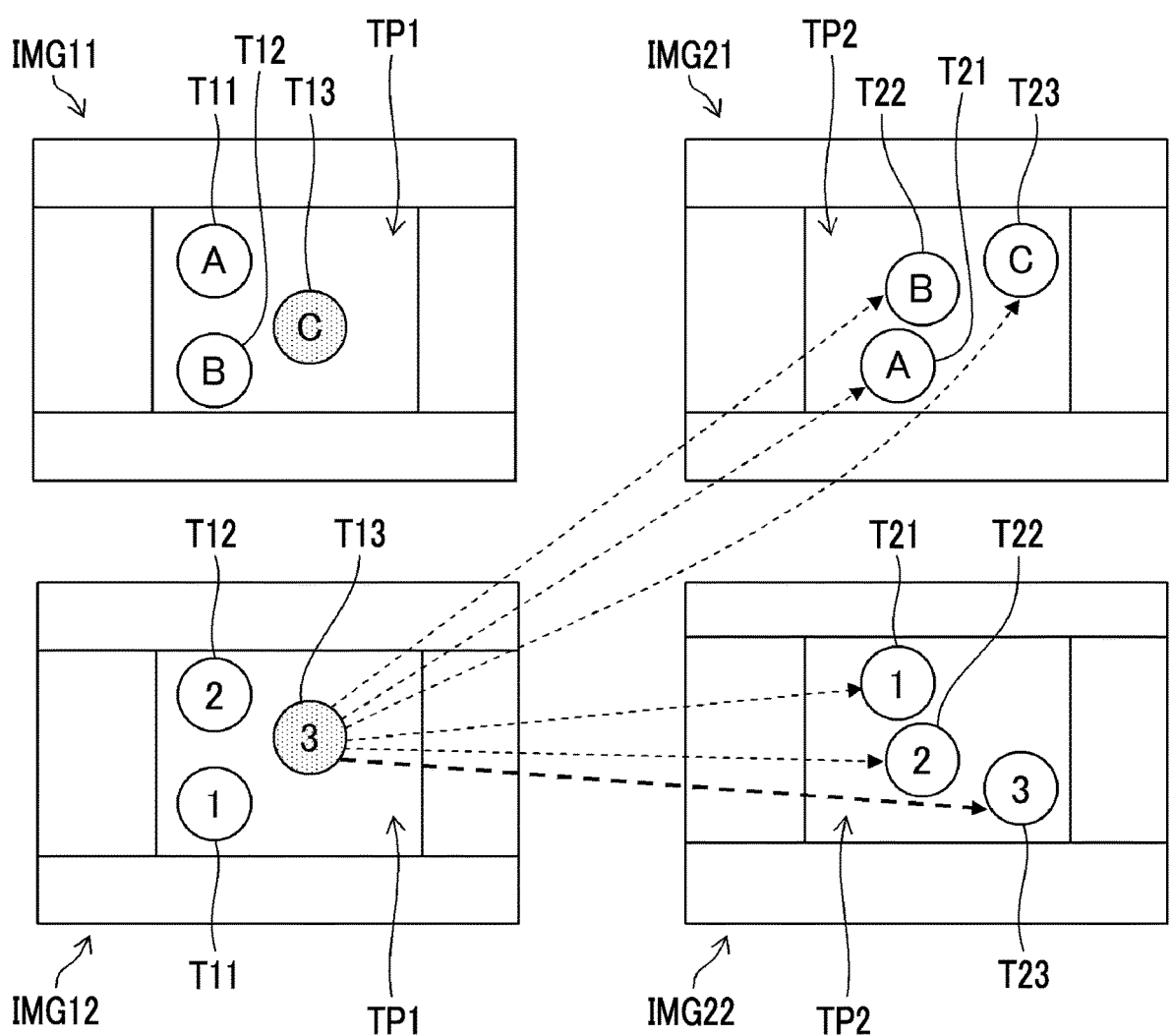
FIG. 10 is a diagram used for description of collating.

As shown in FIG. 3, in a case where the camera 15A and the camera 15B are disposed above or below the drug packages TP that are imaging targets, as shown in FIG. 10, collating is performed using captured images (IMG11 and IMG21) obtained by imaging the drugs T from above using the camera 15A and captured images (in this example, IMG12 and IMG22) obtained by imaging the drugs T from below using the camera 15B. In FIG. 10, in a case where a master image of a type ("type C") of a drug T13 among drugs T11, T12, and T13 in a first drug package TP1 is not registered in the storage unit 18, the image of the drug having a sign T13 (in this example, a drug area of the captured image IMG11 obtained by imaging the drug T13 from above and a drug area of the captured image IMG12 obtained by imaging the drug T13 from below) is registered in the storage unit 18 using the registration unit 46 as the master image. For example, a master image obtained by viewing the drug T13 in the first drug package TP1 from below is collated with images of drugs T21, T22, and T23 in the captured image IMG21 obtained by imaging a second drug package TP2 from above and images of the drugs T21, T22, and T23 in the captured image IMG 22 obtained by imaging the second drug package TP2 from below, as indicated by dashed-line arrows in the figure. For example, it is collated that the image obtained by viewing the drug having a sign T23 in the second drug package TP2 from below matches the master image.

Variation of Master Image

Variation of a master image will be described.
In a case where the same kind of plural drugs T are imaged from one drug package TP (for example, a first drug package) among a plurality of drug packages TP, the master image generating unit 36 may generate a master image using a plurality of drug areas where the same kind of drugs T are imaged. For example, the master image generating unit 36 generates the master image using an average or a weighted average, using the plurality of drug areas.

Further, in a case where the same kind of plural drugs T are imaged over the plurality of drug packages TP as shown in FIG. 2, the master image generating unit 36 generates a master image using drug areas (a plurality of drug areas) in a plurality of captured images corresponding to the plurality of drug packages TP. For example, the master image generating unit 36 generates the master image using an average or a weighted average, using the plurality of drug areas. A configuration in a case where only one of the same kind of drugs T is imaged from one drug package (for example, the first drug package), a master image is generated from an area of one drug T may be used. Further, in a case where the same kind of plural drugs T are not imaged over the plurality of drug packages TP, a master image may be generated from an area of one drug T.

Further, it is preferable that the master image generating unit 36 stores a master image before updating without deleting the master image in updating the master image and uses the master image before updating in generating a new master image.

Illumination Direction Switching

A drug recognizing aspect for sequentially switching illumination directions for a drug will be described. The illumination controller 32 of this aspect switches a light source for illuminating a drug among a plurality of light sources, to thereby sequentially switch an illumination direction for the drug. The imaging controller 34 of this aspect causes the imaging unit 14 to image the drug whenever the illumination direction for the drug is switched. The master image generating unit 36 of this aspect composes a plurality of captured images corresponding to the plurality of illumination directions to generate a master image. According to this aspect, it is possible to accurately recognize an engrave-marked character given to a drug without being affected by the illumination direction in which the drug is illuminated and a surface shape of the drug.

Figure 11:
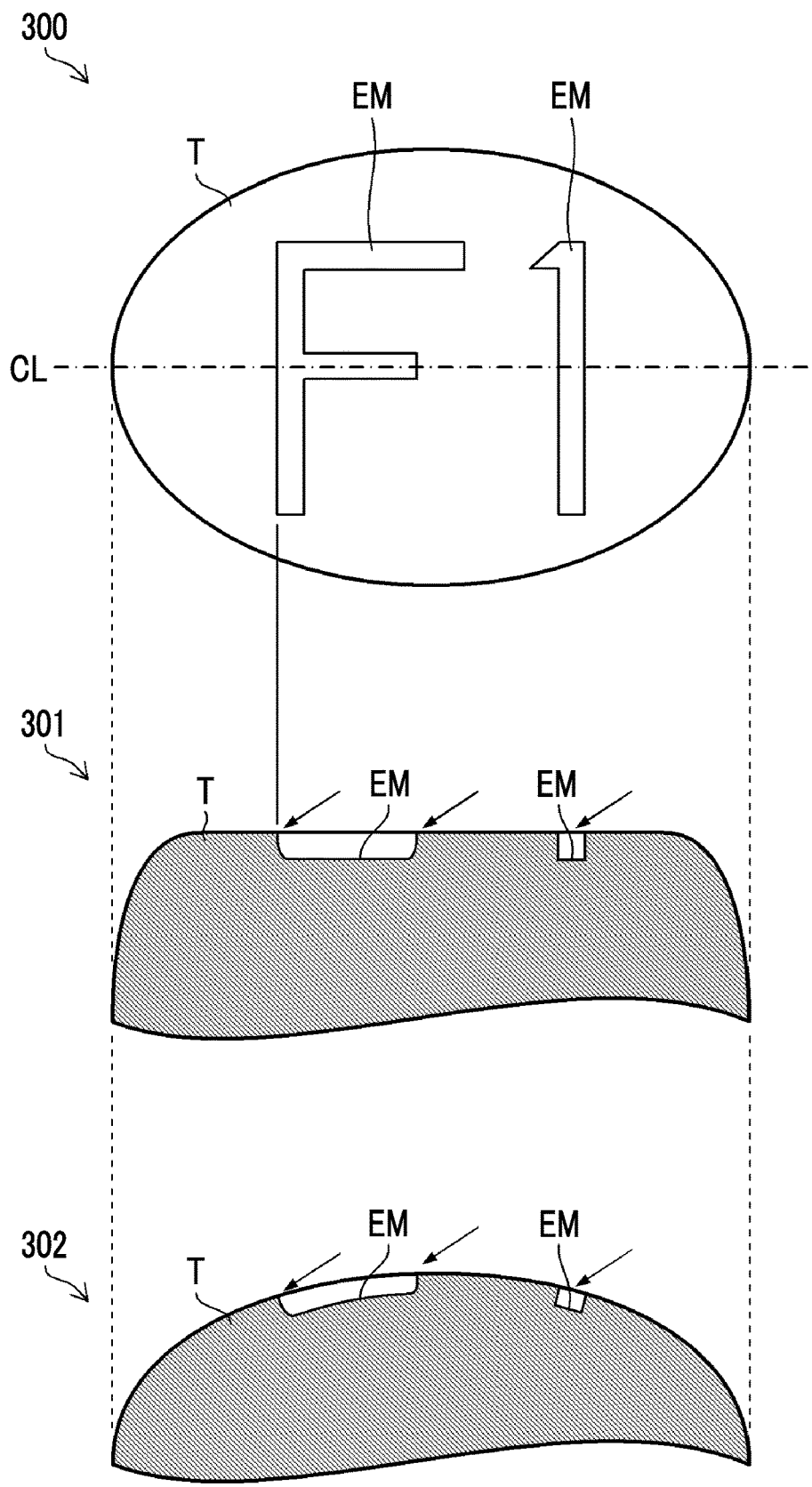
FIG. 11 is a first diagram used for description of illumination direction switching.

As shown in FIG. 11, engraved marks EM are formed by grooves formed on a front surface of the drug T. A reference numeral 300 in the figure indicates a front view of the engraved marks EM, a reference numeral 301 indicates a sectional view of the drug T along a straight line CL in the figure, and a reference numeral 302 indicates a sectional view of the drug T having a surface shape different from that in the sectional view of the reference numeral 301. In a case where the engraved marks EM are illuminated in one direction, shadows are generated along contours of the engraved marks EM on an illumination light source side. Directions, shapes, and intensities of the shadows are changed in accordance with an illumination direction, shapes of the engraved marks EM, and a surface shape of the drug T.

Figure 12:
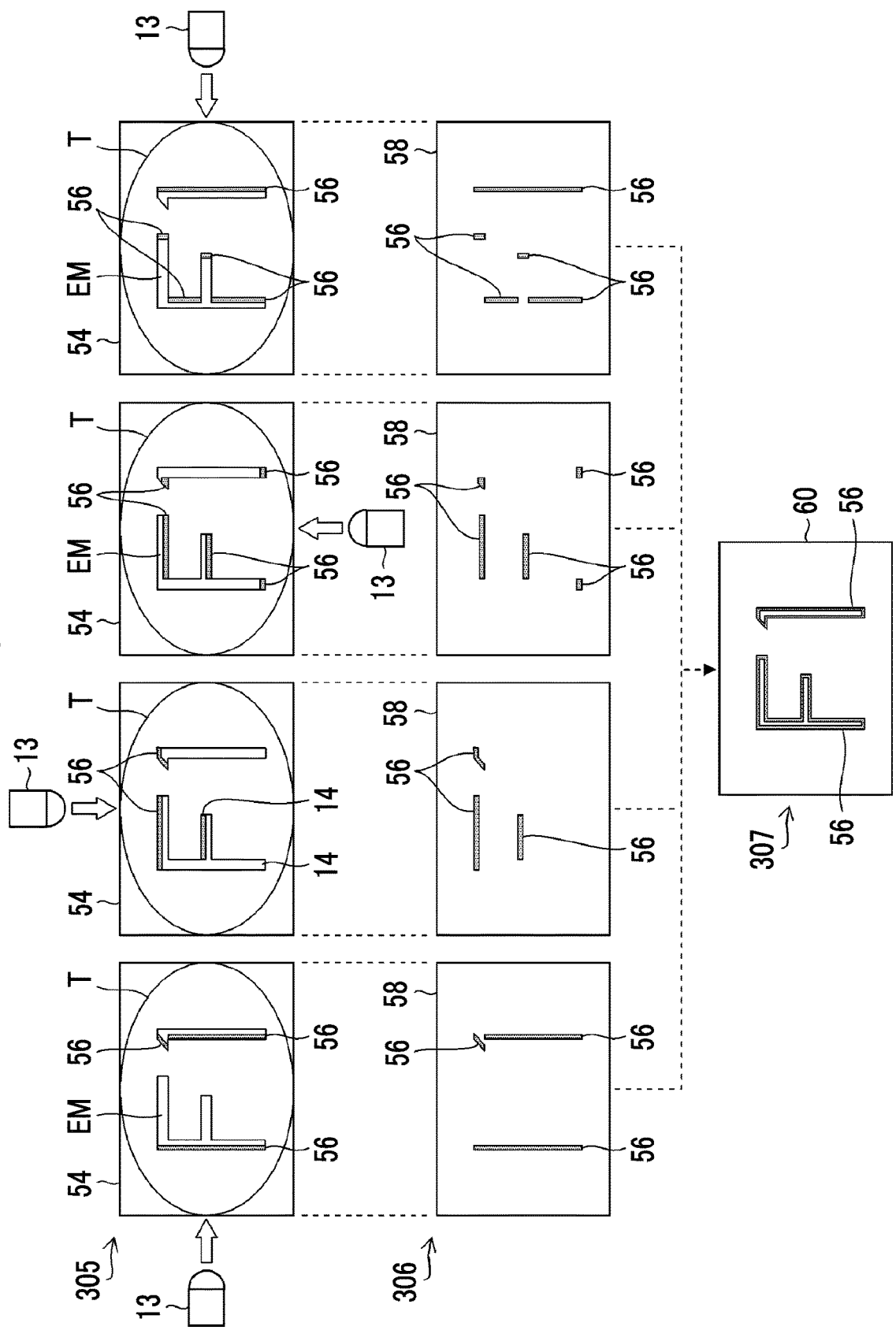
FIG. 12 is a second diagram used for description of the illumination direction switching.

As shown in an upper portion (reference numeral 305) of FIG. 12, shadow images 56 are generated along contours of the respective engraved marks EM on the illumination light source side (on the side of the light source 13 that emits illumination light) in pieces of drug area image data 54 in four directions. The engraved marks EM have the same color as that of the front surface of the drug T, and thus, are not easily identified on actual images, but in order to describe relationships between the engraved marks EM and the shadow images 56 along the illumination directions in the figure, the engraved marks EM are shown to be identifiable.

As shown in a middle portion (reference numeral 306) in FIG. 12, an edge detection process is performed with respect to the pieces of drug area image data 54 in four directions for each drug T, respectively, to extract a piece of feature image data 58 corresponding to the respective shadow images 56 from each piece of drug area image data 54. Thus, with respect to each of the drugs T corresponding to one-time dose, the pieces of feature image data 58 in four illumination directions (hereinafter, referred to as the pieces of feature image data 58 in four directions) are obtained, and the pieces of feature image data 58 in four directions for each drug T are sequentially stored in the storage unit 18.

As shown in a lower portion (reference numeral 307) in FIG. 12, the pieces of feature image data 58 in four directions for each drug T corresponding to one-time dose are read from the storage unit 18, and the pieces of feature image data 58 in four directions for each drug T are integrated to generate integrated image data 60. For example, the pieces of feature image data 58 in four directions are integrated in an overlapping manner. Thus, since the shadow images 56 in four illumination directions are integrated to one, in the piece of integrated image data 60, all contours of the engraved marks EM become clear. Further, the piece of integrated image data 60 is generated for each of the drugs T corresponding to one-time dose, and each piece of integrated image data 60 is stored in the storage unit 18.

Display Control

The display controller 48 has a function for causing the display unit 22 to display drug areas cut out from captured images in parallel. Further, the display controller 48 has a function for causing the display unit 22 to display correlation values calculated by the correlation value calculation unit 49.

FIG. 13 is a diagram showing a display example of a result obtained by recognizing the drugs in the drug packages TP of the package bandage PB shown in FIG. 2. In the example of FIG. 13, images of drugs of an engraved mark "A", images of drugs of an engraved mark "B", and images of drugs of an engraved mark "C" are displayed on the display unit 22, as drugs T recognized from a first drug package TP and a second drug package TP of the package bandage PB. Further, an image of a drug of the engraved mark "B" and an image of a drug of the engraved mark "C" are displayed on the display unit 22, as a drug T recognized from a third drug package TP. Numerical values under the images of the respective drugs represent correlation values calculated by the correlation value calculation unit 49, which are correlation values indicating correlations between images of drug areas extracted from the captured images and master images. Further, the displayed drug areas (drug images) are actually given colors of concentrations depending on the correlation values. With respect to the correlation values of the images of the drugs of the engraved mark "C", it can be understood that since its master image is updated in drug recognition of the first drug package TP, the correlation values in the second and third drug packages become higher than the correlation value in the first drug package.

Further, the display controller 48 has a function for causing the display unit 22 to display a history relating to updating of the master images.

In addition, the display controller 48 has a function for causing the display unit 22 to display positions of drugs (absolute positions or relative positions) and updating of the master images in association.

Processing Example

Figure 14:
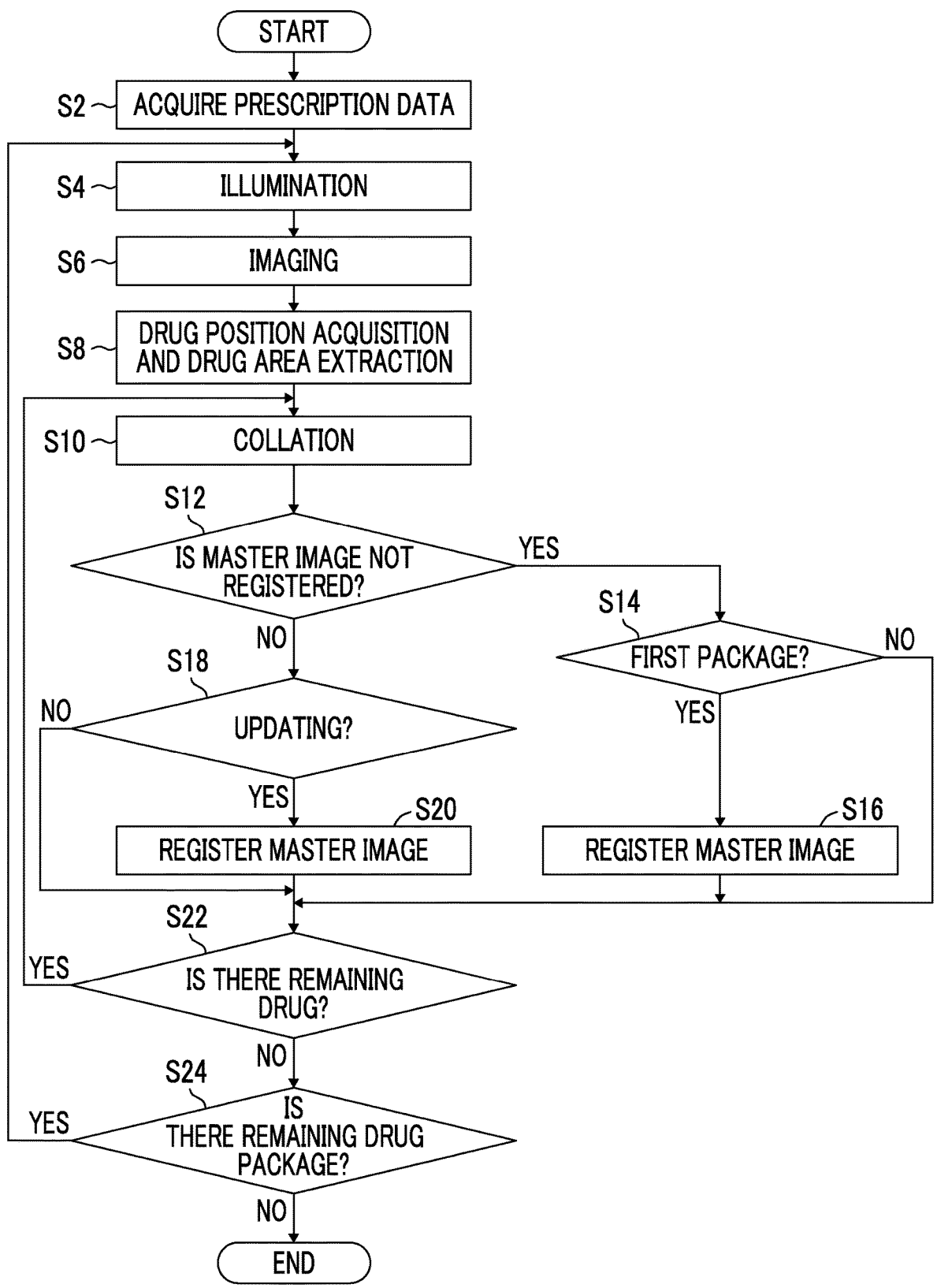
FIG. 14 is a flowchart showing a flow of a processing example to which a drug recognizing method according to the present invention is applied.

FIG. 14 is a flowchart showing a flow of a processing example to which the drug recognizing method according to the present invention is applied. This process is executed by a CPU that forms the processing unit 20 of the drug recognizing apparatus 10 in accordance with a program (including the drug recognizing program according to the present invention).

First, the above-described associated information such as prescription data is acquired by the associated information acquiring unit 16 (step S2).

Then, dividedly packaged drugs are illuminated by the illumination unit 12 (step S4).

Further, the drugs illuminated by the illumination unit 12 are imaged by the imaging unit 14 (step S6).

Then, drug positions are acquired by the drug position acquiring unit 35, and drug areas are extracted from captured images by the master image generating unit 36 (step S8).

Master images stored in the storage unit 18 and the drug areas in the captured images are collated with each other by the collation unit 42 (step S10).

Then, it is determined whether there is a drug of which a master images is not registered in the storage unit 18 (step S12), and in a case where there is the drug of which the master image is not registered (YES in step S12), it is determined whether the drug is in the first package (step S14). In a case where the master image is not registered and the drug is in the first package (YES in step S14), an image of a drug area extracted from a captured image is registered as a master image by the registration unit 46 (step S16).

In a case where there is no drug of which the master image is not registered (NO in step S12), it is determined by the updating determination unit 44 whether to update the master images on the basis of distances between a reference position in an imaging range (for example, a central position) and the positions of the drugs (step S18).

In a case where it is determined that the master images are to be updated (YES in step S18), the images of the drug areas extracted from the captured images are registered as master images by the registration unit 46 (step S20).

It is determined whether there is a remaining drug in the drug package (step S22), and in a case where there is the remaining drug in the drug package (YES in step S22), the procedure returns to step S10, and the collation process is performed with respect to the remaining drug in the drug package.

In a case where the drug recognition process is performed with respect to all drugs in the drug package and there is no remaining drug (NO in step S22), it is determined whether there is a remaining drug package (step S24), and in a case where there is the remaining drug package, the procedure returns to step S4.

In a case where a plurality of drugs are included in one drug package, the updating determination unit 44 may determine whether to update the master images on the basis of intervals of the plurality of plural drugs. That is, in the case of engraved marks, in a case where a large drug is present in the vicinity, there is a case where shadows do not easily occur, and thus, it is preferable to determine that the master images are to be updated in a case where other drugs are not present in the vicinity. For example, in a case where a distance between drugs is smaller than a threshold (or equal to or smaller than the threshold), since the shadows of the engraved marks do not easily occur in the captured images, it is determined that the master images are not to be updated.

In the above description, a case where engraved marks of drugs are recognized has been mainly described as an example, but characters or signs printed in the drugs may be recognized.

Further, the above-described processing unit 20 shown in FIG. 1 may be configured to include a variety of processors as described later. The variety of processors plurality includes a central processing unit (CPU) that is a general-purpose processor that executes a variety of processes using software (program), a programmable logic device (PLD) that is a processor of which a circuit configuration is changeable after manufacturing, such as a field-programmable gate array (FPGA), a dedicated electric circuit that is a processor having a circuit configuration that is dedicatedly designed for executing a specific process, such as an application specific integrated circuit (ASIC), or the like. In the above-described embodiments, the functions of the processing unit 20 may be realized by one processor among the variety of processors, or may be realized by the same or different two or more processors (for example, a combination of a plurality of FPGAs, or a combination of CPU and FPGA). Further, a plurality of functions may be realized by one processor. As an example in which the plurality of functions are realized by one processor, there is a configuration in which a processor that realizes entire functions of a system including the plurality of functions by one integrated circuit (IC) chip, as represented as a system-on-chip (SoC) or the like, is used. As described above, the variety of functions may be realized by using one or more various processors described above as a hardware structure. Further, more specifically, the hardware structure of the various processors is an electric circuitry in which circuit elements such as semiconductor elements are combined.

In a case where the above-described processor or electric circuitry executes software (program), processor (computer)-readable codes of the software to be executed are stored on a non-temporary recording medium such as a read only memory (ROM) and/or a flash memory ROM, and the processor refers to the software. The software that is stored on the non-temporary recording medium includes a program (drug recognizing program) for executing the drug recognizing method according to the present invention. The codes may be stored on a non-temporary recording medium such as a variety of magneto-optical recording apparatuses, or a semiconductor memory, instead of the ROM. In the case of processing using the software, a video RAM (VRAM), or a synchronous dynamic random access memory (SDRAM) is used as a temporary storage area, and for example, data stored in an electronically erasable and programmable read only memory (EEPROM) (not shown) may be also referred to.

The above-described drug recognizing apparatus may be applied to a check supporting apparatus that supports a drug compounding check, a one-packaging apparatus that packages drugs for one-time dose, a drug differentiation apparatus that differentiates drugs, or an ingestion support apparatus that supports ingestion of drugs, for example. The drug recognizing apparatus may be applied to other types of apparatuses. The above-described drug recognizing method may be executed in accordance with the drug recognizing program using the computer apparatus, the check supporting apparatus, the one-packaging apparatus, the drug differentiation apparatus, the ingestion supporting apparatus, or the like.

Application Example of Drug Check Support and Drug Differentiation

Figure 15:
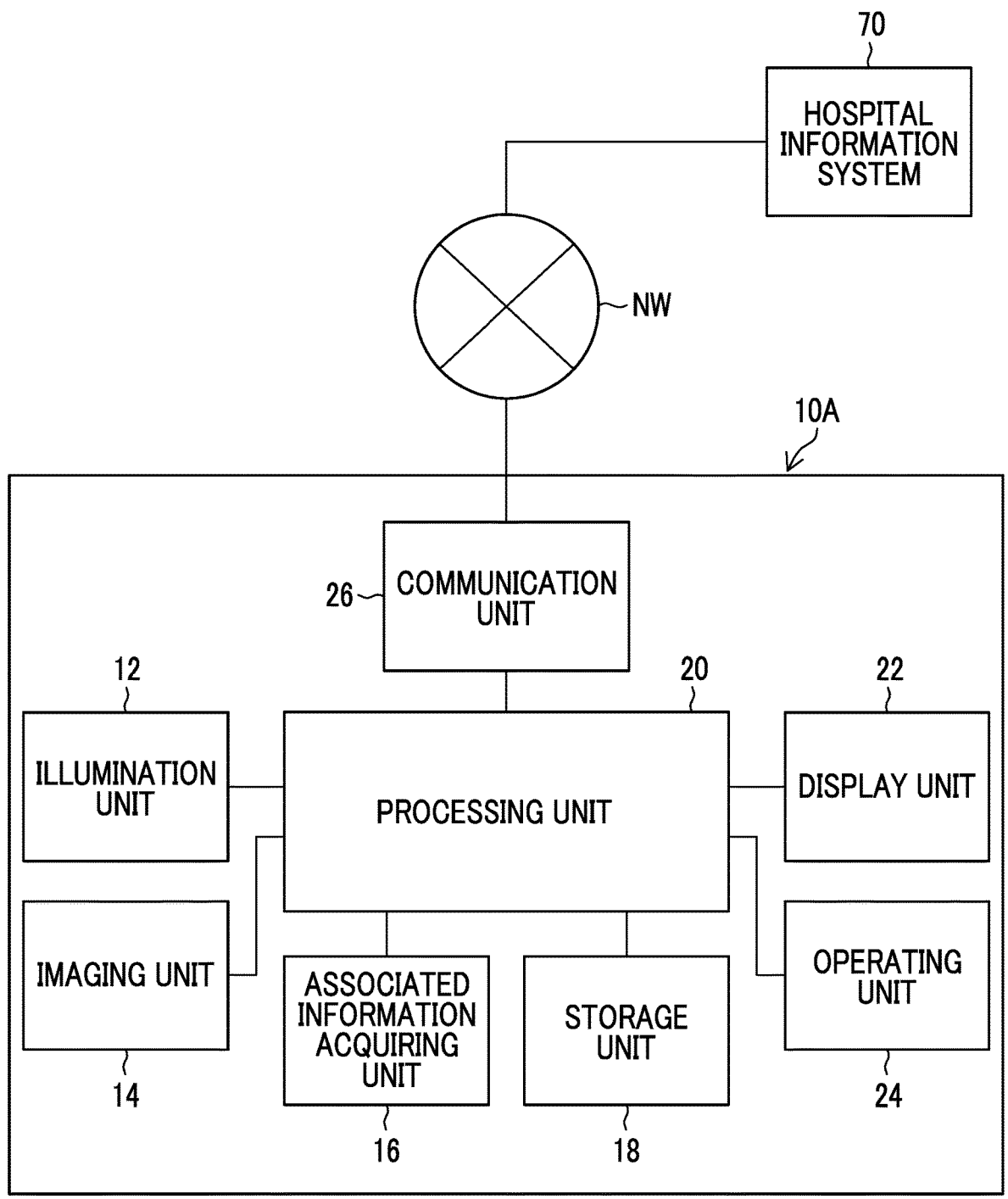
FIG. 15 is a diagram showing an example of a system in which the drug recognizing apparatus according to the present invention is applied to drug inspection support and drug differentiation.

An example in which the above-described drug recognizing apparatus, drug recognizing method and drug recognizing program are applied to drug check support and drug differentiation will be described. FIG. 15 is a diagram showing a system in which a drug recognizing apparatus 10A (drug check supporting apparatus, drug differentiation apparatus) is connected to a hospital information system 70 through a network NW. Other apparatuses (one packaging apparatus, ingestion supporting apparatus, or the like) may be connected to the network NW.

The drug recognizing apparatus 10A is provided with a communication unit 26, and is able to communicate with the hospital information system (HIS) 70 through the communication unit 26 and the network NW. Since other configurations are equal to those of the above-described drug recognizing apparatus 10, the same reference numerals are given to the same configurations, and description thereof will not be repeated. A specific configuration of the processing unit 20 is equal to that shown in FIG. 1.

Figure 16:
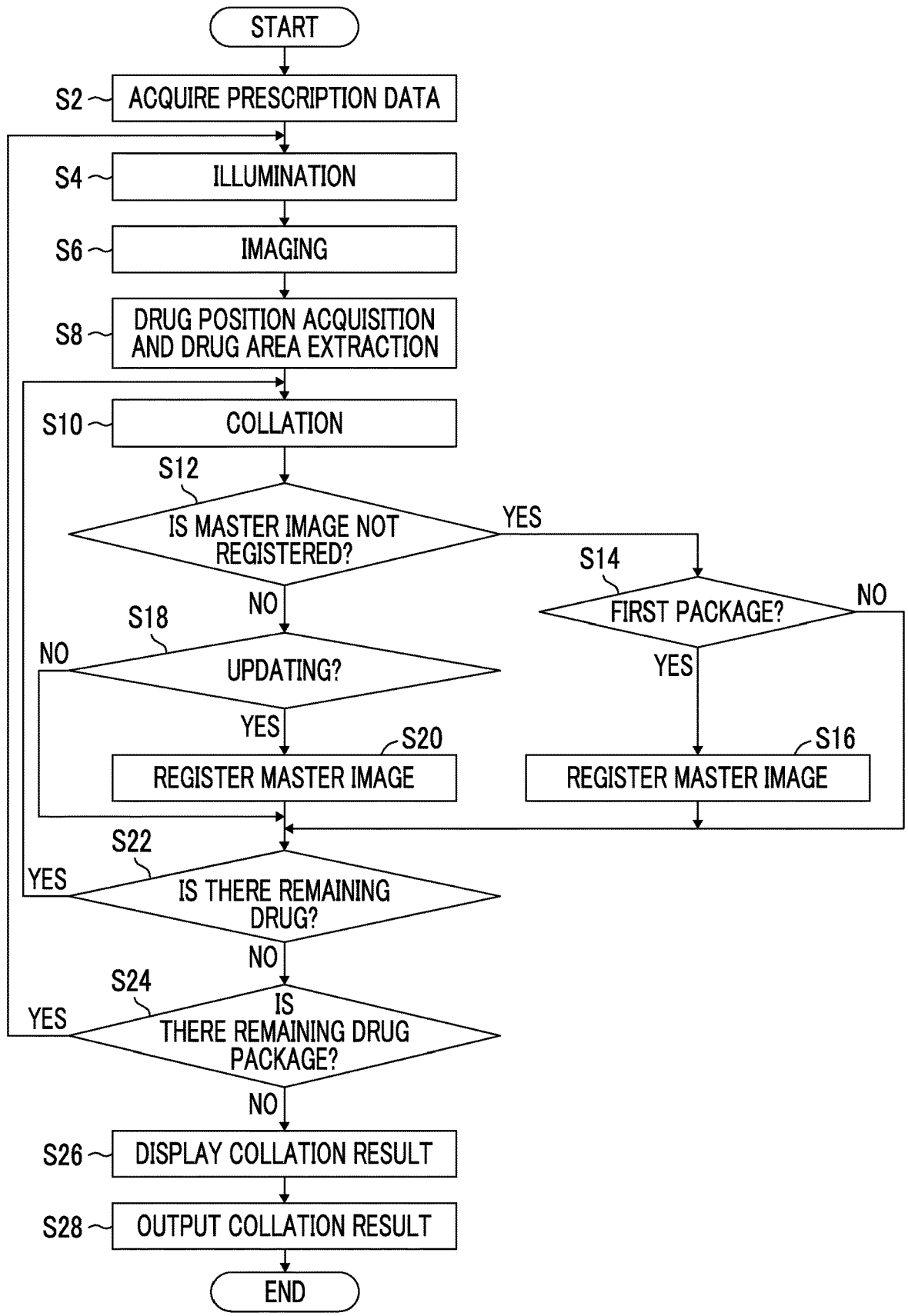
FIG. 16 is a flowchart showing a flow of a processing example in which the drug recognizing method according to the present invention is applied to the drug inspection support.

FIG. 16 is a flowchart showing processes of a drug check supporting method using the drug recognizing apparatus 10A. Processes from step S2 to step S24 are equal to the steps in the flowchart of FIG. 14, and the collation unit 42 (drug determination unit, determination result output unit, see FIG. 1) collates a master image with a collation target image (an image in a drug area extracted from a captured image) in step S10, and the display controller 48 (determination result output unit, see FIG. 1) displays the collation result in step S26. The master image used in the collation of step S10 is a master image that is finally registered in step S16 or step S20.

Figure 17:
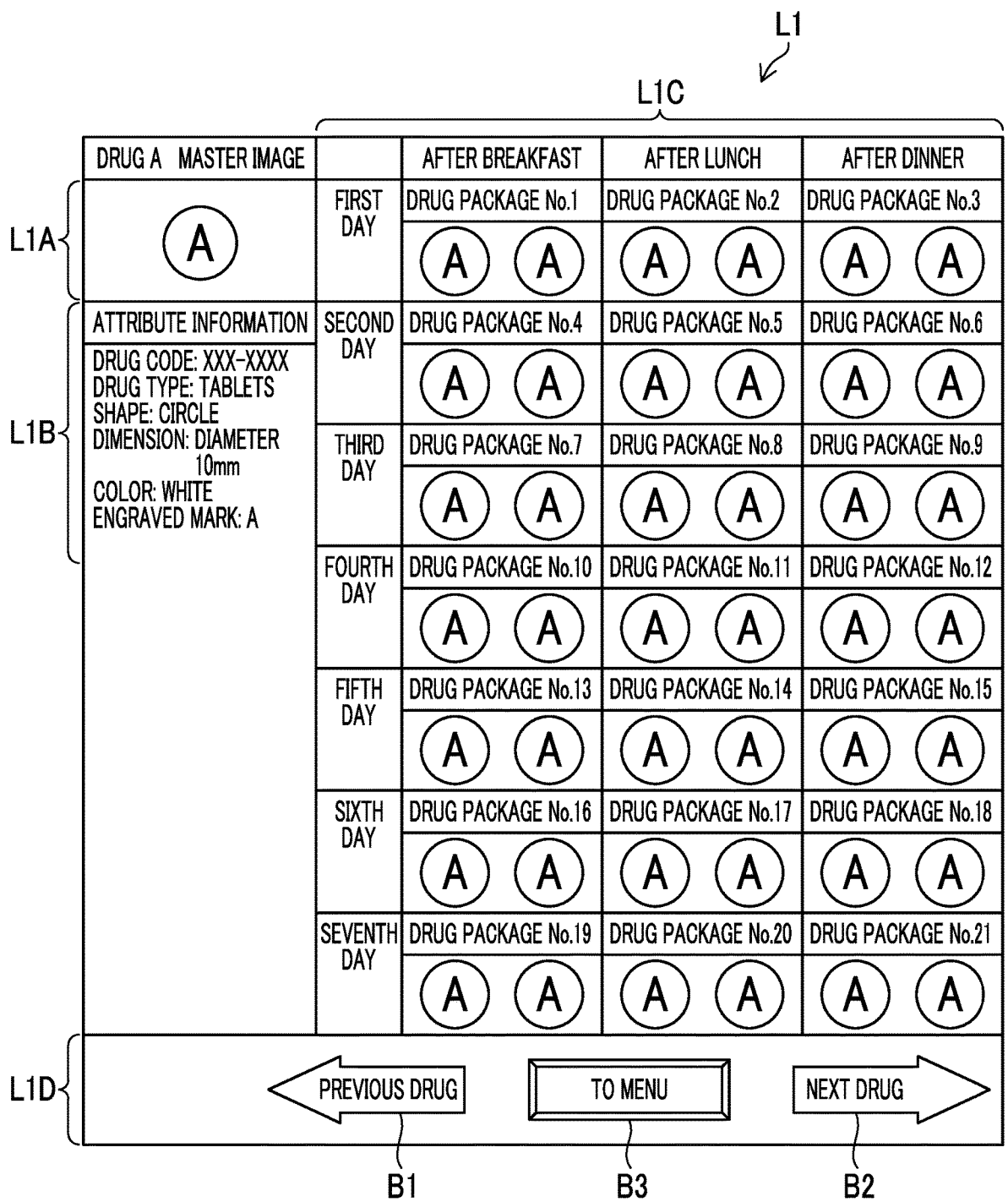
FIG. 17 is a diagram showing an example of a result obtained by applying the drug recognizing method and apparatus according to the present invention to the drug inspection support.

FIG. 17 is a diagram showing a display example (example of a list table L1 of collation results for drugs A) of collation results. In FIG. 17, a master image of the drugs A and attribute information (information indicating an attribute of the drug) are respectively displayed on a left side (areas L1A and L1B) of the list table L1, and all collation target images for which it is determined that "drug A is shown" are displayed on a right side (area L1C). In FIG. 17, the list table L1 includes only an image for a front surface of a drug (face on which an engraved mark is written), but may include an image for a rear surface of the drug. In the area L1C of the list table L1, the collation target images are displayed for each divided package and for each ingestion timing, and inspection support information (information for efficiently performing collation and inspection of drugs) with respect to a drug package TP is displayed together with the collation target images. In the example shown in FIG. 17, the inspection support information includes an ingestion timing, a divided package number, and an ingestion date, but may include different information (similarity between a captured image and a master image, or the like). In the example shown in FIG. 17, it is assumed that the drugs A of two tablets are accurately packaged in all divided packages (three times a day×one week=21 packages) and an ingestion period is seven days.

The collation unit 42 outputs the collation results (step S28). The collation results may be stored in the storage unit 18, or may be transmitted to the hospital information system 70 through the communication unit 26 and the network NW. In view of compatibility of information with respect to the hospital information system 70, the collation results may be output in the form of SS-MIX (Standardized Structured Medical Information eXchange) or SS-MIX2.

In the drug recognizing apparatus 10A, since the master image that is finally registered and the collation target images are collated as described above, it is possible to accurately perform drug recognition and check support using a master image with enhanced robustness.

Figure 18A:
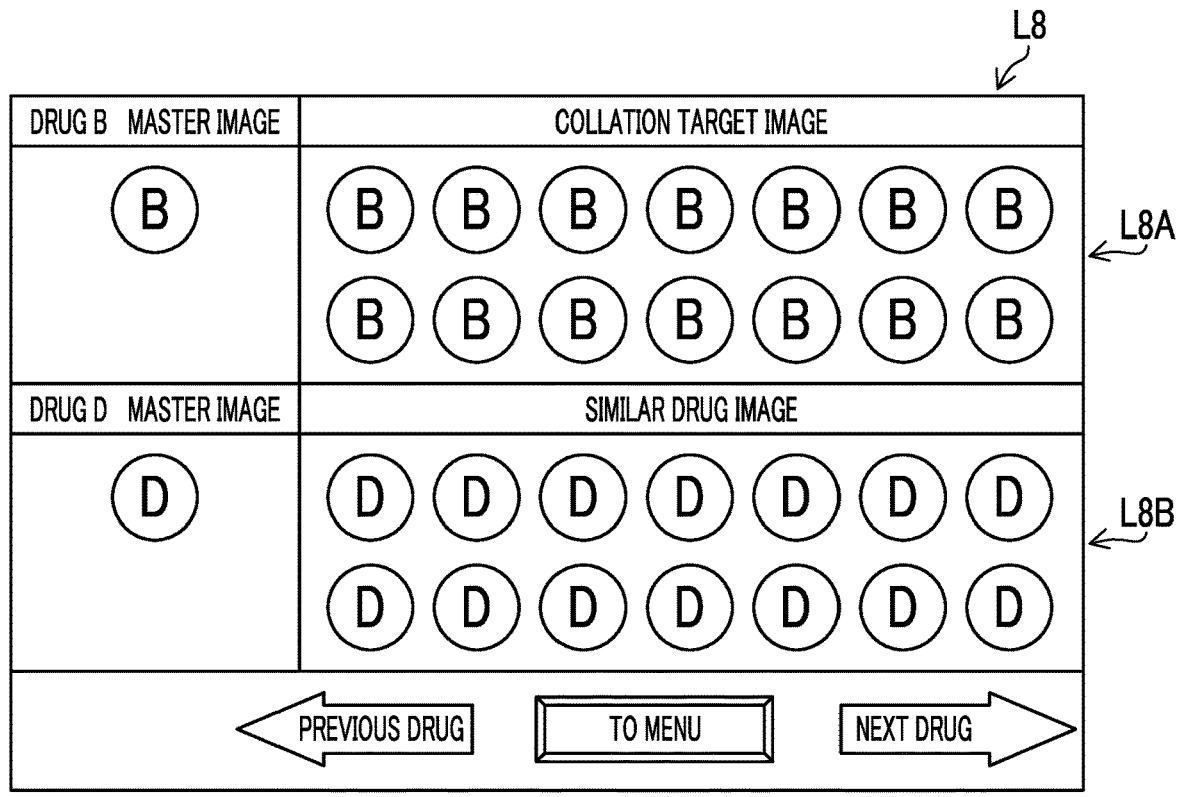
FIG. 18 is a diagram showing another example of a result obtained by applying the drug recognizing method, and apparatus according, to the present invention to the drug inspection support.
Figure 18B:
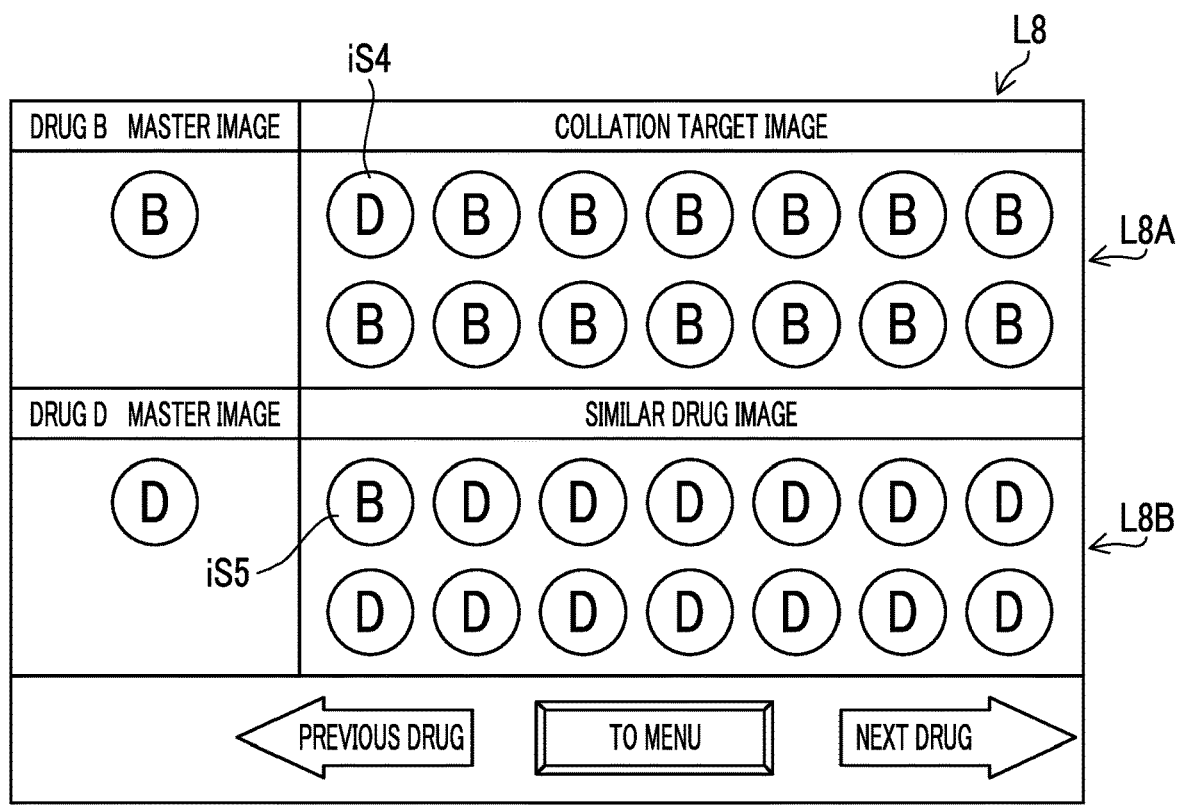

FIG. 18 is a diagram showing a display example of collation results for designated drugs and similar drugs. (a) in FIG. 18 represents a list table L8 including a list table L8A for drugs B and a list table L8B for drugs D that are drugs similar to the drugs B. Further, (b) in FIG. 18 represents a state where a collation error of drugs occurs in the list table L8 (in the list table L8A, a drug D indicated by a collation target image iS4 is determined as a drug B, and contrarily, in the list table L8B, a drug B indicated by a collation target image iS5 is determined as a drug D). Even in a case where similar drugs (drug B and drug D) are replaced with each other due to the collation error as described above, by displaying the list table L8B for the drugs D that are the similar drugs together with the list table L8A for the drugs B, it is possible for a user (pharmacist) to easily notice the collation error. Further, similar to the example shown in FIG. 17, it is possible to accurately perform drug recognition and check supporting using a master image with enhanced robustness.

Figure 19:
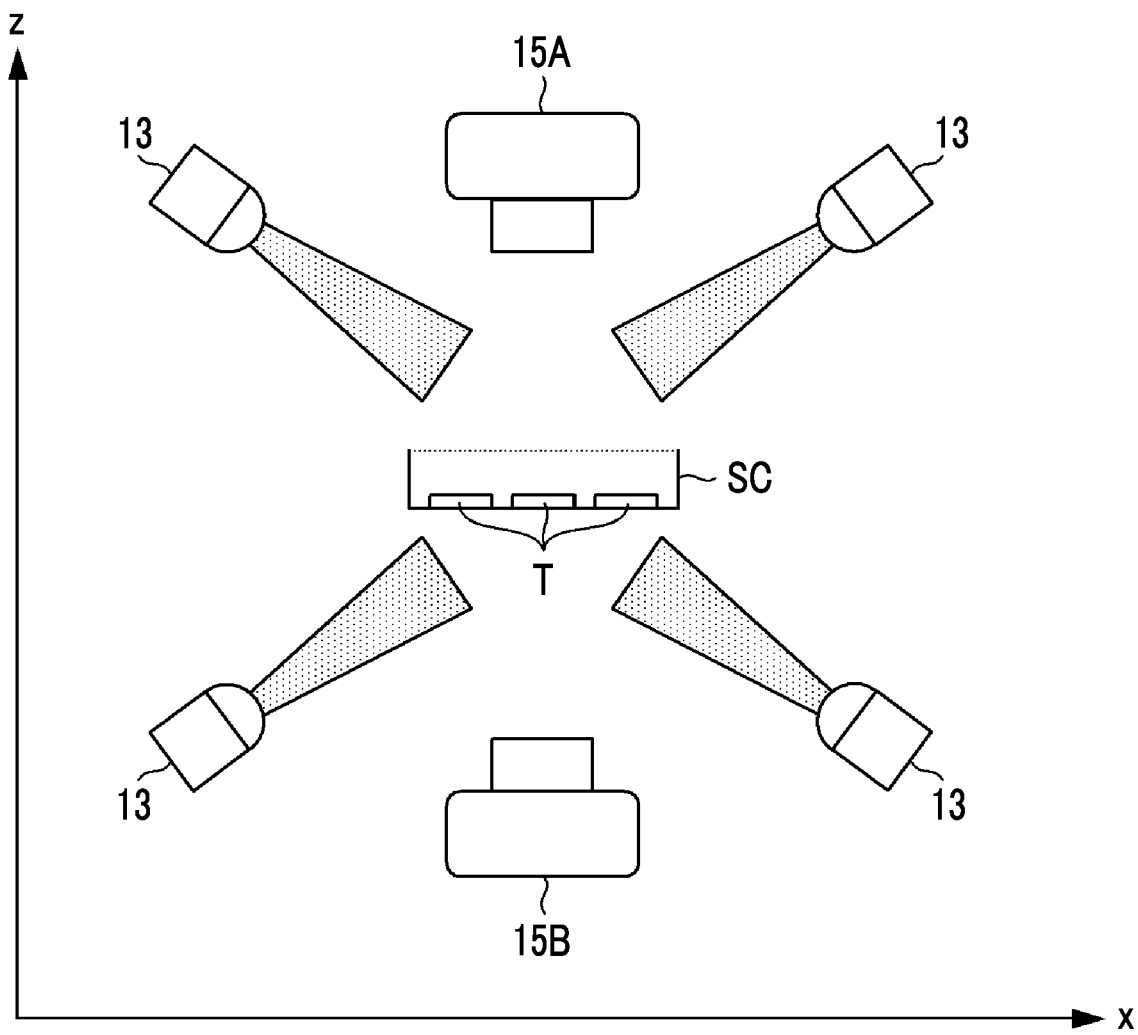
FIG. 19 is a diagram showing an example in which the drug recognizing apparatus according to the present invention is applied to the drug differentiation.
Figure 20:
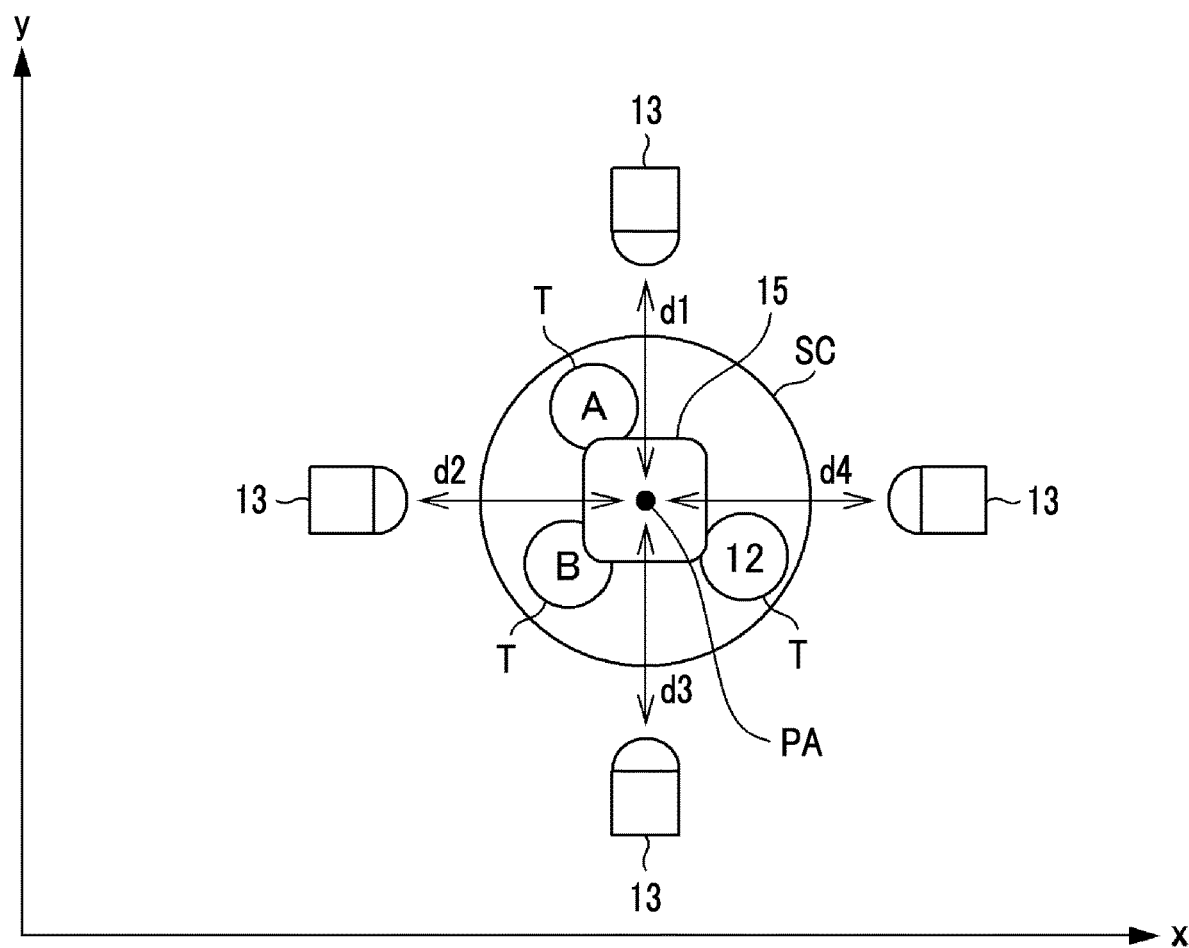
FIG. 20 is a diagram showing the example in which the drug recognizing apparatus according to the present invention is applied to the drug differentiation.

FIG. 19 and FIG. 20 are diagrams showing examples in which differentiation of drugs is performed using the drug recognizing apparatus 10A. The differentiation of the drugs may be performed in a case where a doctor and/or a pharmacist wants to figure out types, quantities or the like of drugs, for example, in a case where a patient carries prescribed drugs to a hospital, a drug store, or the like, or in a case where the doctor and/or the pharmacist visits a patient's home and manages the remaining drugs. However, the present invention is not limited to such a case. In the example shown in FIGS. 19 and 20, the drugs T are put in a schale SC and are placed on a placing table (not shown). In this state, illumination and imaging are performed in a similar way to the example shown in FIG. 3. The drugs T may be directly placed on the placing table without being put in the schale SC, or may be placed in a state of being put in a divided package.

Figure 21:
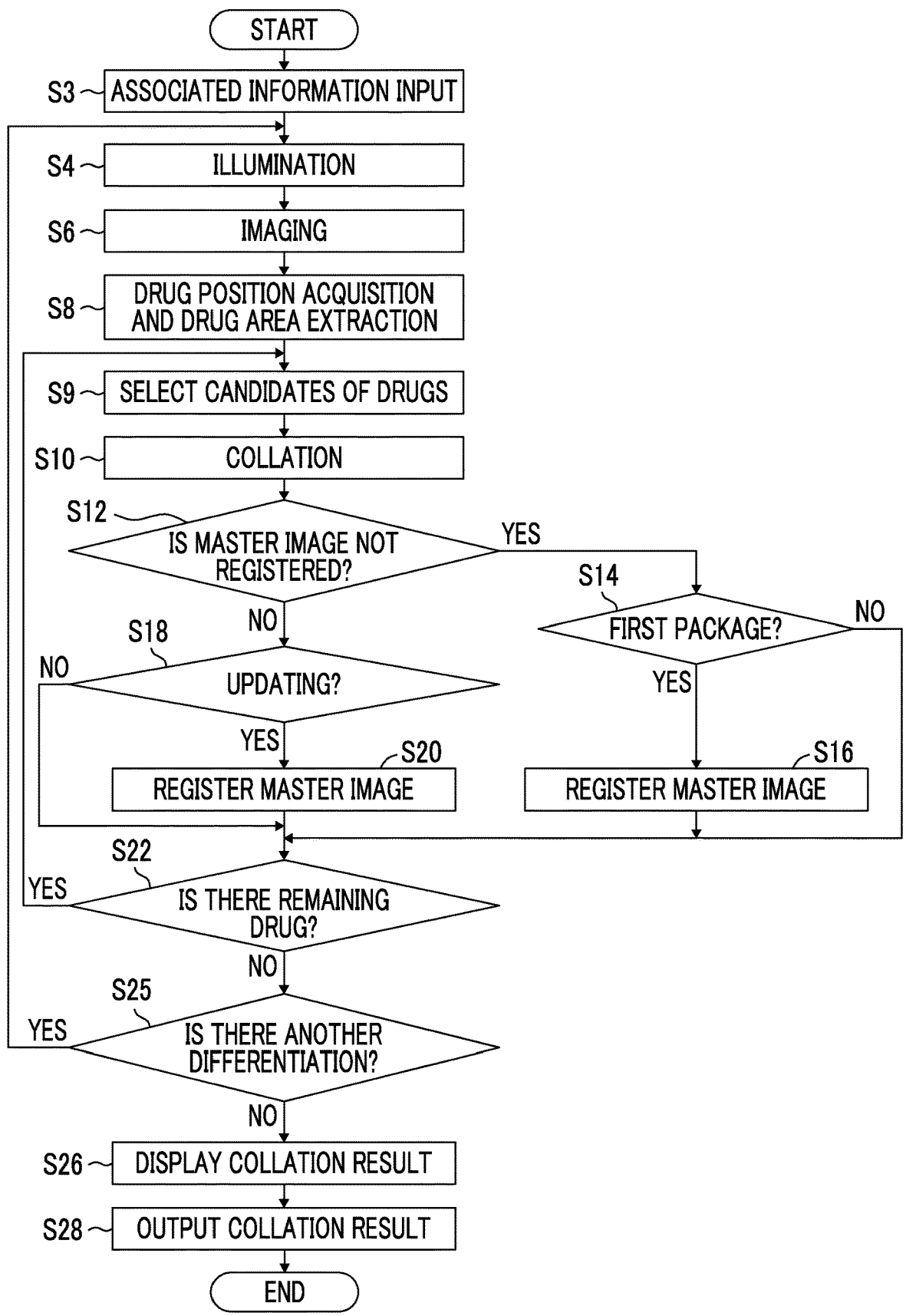
FIG. 21 is a flowchart showing a flow of a processing example in which the drug recognizing method according to the present invention is applied to the drug differentiation.

FIG. 21 is a flowchart showing a processing example of the drug recognizing method using the drug recognizing apparatus 10A. The same step numbers are given to portions indicating the same processes as in the flowcharts of FIGS. 14 and 16, and detailed description thereof will not be repeated. In the example shown in FIG. 21, the associated information acquiring unit 16 (associated information input unit) acquires associated information through an operation of the operating unit 24 from a user (step S3). The collation unit 42 (drug determination unit, determination result output unit) determines what a drug indicated by a captured image is with reference to the acquired associated information. In a situation where drug differentiation is performed, a case where a prescription or prescription data is not present, such as a case where a patient carries drugs that the patient takes to a drug store, may be considered, but in such a case, information on drugs written in a pocketbook such as a so-called "drug history handbook" may be acquired as the associated information. Alternatively, a doctor and/or a pharmacist may acquire and input information (drug types such as tablets or capsules, colors, engraved marks and/or printing, or the like) on drugs that are visually acquired, or the like. Even in a case where effective associated information cannot be obtained, information for specifying patients such as names, genders or ages of inpatients, ward names, or the like may be input, or may be omitted.

The collation unit 42 selects collation targets on the basis of the associated information input in step S3 (step S9). For example, the drugs written in the "drug history handbook" and similar drugs are selected as the collation targets. Alternatively, the collation targets are selected on the basis of drug types, colors, or the like of the drugs that are visually acquired. By selecting the collation targets in this way, it is possible to narrow down a collation range, to thereby rapidly perform differentiation. In a case where the associated information is not input in step S3, the process of step S9 may not be performed.

The collation unit 42 collates collation target images (images of drug areas extracted from captured images) with a master image for the drug that is the collation targets selected in step S9, and selects candidates of drugs indicated by the collation target images (captured images) on the basis of the collation results (step S10). Since the master image used in the collation is a master image that is finally registered in step S16 or S20, recognition and differentiation of drugs may be accurately performed using a master image with enhanced robustness. In a case where the process of step S9 is not performed, collation with master images of all the drugs may be performed.

In a case where the differentiation is terminated (NO in step S25), the display controller 48 (determination result output unit, see FIG. 1) displays the collation results on the display unit 22 (step S26). FIG. 22 is a diagram showing a display example (output example of information indicating candidates of drugs indicated by captured images) of collation results, and displays master images and drug IDs of drugs having high coincidences with respect to drugs of collation targets. Thus, a user can confirm the candidates of the drugs indicated by the captured images. In the display shown in FIG. 22, in accordance with designation of the displayed drugs (for example, through click using a mouse (not shown) of the operating unit 24), the display controller 48 may display a master image and attribute information thereof on the display unit 22 as shown in FIG. 23.

The output (step S28) of the collation results may be performed in a similar way to step S28 of the flowchart in FIG. 16.

The above-described drug check support and differentiation may be performed by an apparatus (one type of the drug recognizing apparatus) such as a personal computer, a smartphone, or a tablet terminal. For example, the drug recognizing program that executes the processes of the drug recognizing method according to the present invention may be installed in such an apparatus, and a captured image by imaging of a drug using an internal camera in the apparatus and/or an externally attached camera may be collated with a master image. The processes of drug recognition, check support, and differentiation may be performed by the above-described apparatus, or may be performed by receiving results obtained by processing information input to the apparatus on a network, or by a server on a cloud, or the like.

Hereinabove, the embodiments for executing the present invention have been described, but the present invention is not limited to the above-described embodiments and modification examples, and various modifications made be made in a range without departing from the concept of the present invention.

EXPLANATION OF REFERENCES

10: drug recognizing apparatus
10A: drug recognizing apparatus
12: illumination unit
13: light source
14: imaging unit
15 (15A, 15B): camera
16: associated information acquiring unit
18: storage unit
20: processing unit
22: display unit
24: operating unit 26: communication unit
32: illumination controller
34: imaging controller
35: drug position acquiring unit
36: master image generating unit
42: illumination unit
44: updating determination unit
46: registration unit
48: display controller
49: correlation value calculation unit
50: reference position setting unit
54: drug area image data
56: shadow image
58: feature image data
60: integrated image data
70: hospital information system
A: drug
AR: area
B: drug
D: drug
EM: engraved mark
LI: incident light
L: brightness profile
LO: reflecting light
NW: network
PA: imaging optical axis
PB: package bandage
PI: attention position
R: imaging range
RQ: quarter area
SC: schale
T, T11, T12, T13, T21, T22, T23: drug
TE, TR: drug
TP (TP1, TP2): drug package

What is claimed is:

1. A drug recognizing apparatus comprising:
an illumination unit that illuminates a drug;
an imaging unit that images the drug illuminated by the illumination unit;
a storage unit that stores a master image showing the drug for each drug type;
a drug position acquiring unit that acquires a position of the drug on the basis of a captured image obtained by the imaging unit;
an updating determination unit that determines whether to update the master image on the basis of the position of the drug acquired by the drug position acquiring unit;
a master image generating unit that generates the master image from a drug area in the captured image obtained by the imaging unit; and
a registration unit that registers the master image generated by the master image generating unit in the storage unit in a case where the updating determination unit determines that the master image is to be updated,
wherein the registration unit stores drug position information indicating the position of the drug in association with the master image in the storage unit, and
wherein the updating determination unit determines whether to update the master image on the basis of the position of the drug imaged by the imaging unit and the drug position information associated with the master image.

2. The drug recognizing apparatus according to claim 1, wherein the updating determination unit determines that the master image is to be updated in a case where cognitive power for the drug at the position of the drug imaged by the imaging unit is higher than that at the position of the drug in the master image indicated by the drug position information associated with the master image.

3. The drug recognizing apparatus according to claim 2, wherein in a case where a type of drug of which the master image is not registered is imaged by the imaging unit, the registration unit registers the drug area in the captured image obtained by the imaging unit as the master image in the storage unit.

4. The drug recognizing apparatus according to claim 1, wherein the updating determination unit determines whether to update the master image on the basis of a distance between a reference position at which cognitive power for the drug in an imaging range of the imaging unit satisfies a criterion and the position of the drug.

5. The drug recognizing apparatus according to claim 4, wherein the illumination unit illuminates the drug in a plurality of illumination directions surrounding the drug,
wherein the imaging unit faces at least one face of a packaging member that wraps the drug,
wherein the reference position is a central position in the imaging range, and
wherein the updating determination unit determines whether to update the master image on the basis of a distance between the central position in the imaging range and the position of the drug.

6. The drug recognizing apparatus according to claim 4, further comprising
a reference position setting unit that calculates in advance the position at which the cognitive power for the drug in the imaging range of the imaging unit satisfies the criterion, and sets the calculated position as the reference position.

7. The drug recognizing apparatus according to claim 4, wherein the reference position is a position at which the cognitive power for the drug in the imaging range is the highest or a representative position in an area at which the cognitive power for the drug is the highest.

8. The drug recognizing apparatus according to claim 2, wherein the cognitive power is cognitive power for an engraved mark on a front surface of the drug, and is determined in accordance with an incident angle at which illumination light of the illumination unit is incident to the engraved mark on the front surface of the drug.

9. The drug recognizing apparatus according to claim 5, wherein the illumination unit is configured to include a plurality of light sources, and the plurality of light sources and an optical axis of the imaging unit are disposed at equal intervals.

10. The drug recognizing apparatus according to claim 1, wherein the illumination unit illuminates the drug in four or more directions.

11. The drug recognizing apparatus according to claim 1, wherein the updating determination unit determines whether to update the master image on the basis of intervals of the plurality of drugs in a case where a plurality of the drugs are included in one drug package.

12. The drug recognizing apparatus according to claim 1, wherein the illumination unit is configured to include a plurality of light sources,
wherein the drug recognizing apparatus further comprises:

an illumination controller that sequentially switches an illumination direction of the drug by switching the light source that illuminates the drug among the plurality of light sources; and an imaging controller that causes the imaging unit to image the drug whenever the illumination direction is switched, and wherein the master image generating unit composes the plurality of captured images corresponding to the plurality of illumination directions, obtained by the imaging unit, to generate the master image.

13. The drug recognizing apparatus according to claim 1, wherein the imaging unit is configured to include a first camera that images the drug in a first direction and a second camera that images the drug in a second direction different from the first direction.

14. The drug recognizing apparatus according to claim 1, wherein the drug is packaged.

15. The drug recognizing apparatus according to claim 1, wherein a plurality of drug packages in which the drug is packaged are continuous, and wherein in a case where the same kind of plural drugs are imaged from one drug package, or in a case where the same kind of plural drugs are imaged over the plurality of drug packages, the master image generating unit generates the master image using a plurality of drug areas in which the same kind of plural drugs are imaged.

16. The drug recognizing apparatus according to claim 15, wherein in a case where the same kind of plural drugs are imaged from one drug package, or in a case where the same kind of plural drugs are imaged over the plurality of drug packages, the master image generating unit generates the master image using an average or a weighted average using the plurality of drug areas.

17. The drug recognizing apparatus according to claim 1, further comprising:

a display unit; and a display controller that causes the display unit to display the drug area in the captured image.

18. The drug recognizing apparatus according to claim 17, further comprising a correlation value calculation unit that calculates a correlation value between the master image and the drug area in the captured image, wherein the display controller causes the display unit to display the correlation value.

19. The drug recognizing apparatus according to claim 17, wherein the display controller causes the display unit to display a history of the updating of the master image.

20. The drug recognizing apparatus according to claim 19, wherein the display controller causes the display unit to display the position of the drug and the updating of the master image in association.

21. The drug recognizing apparatus according to claim 1, further comprising:

a drug determination unit that collates a master image that is finally registered among the master images registered in the storage unit with the captured image to determine what the drug indicated by the captured image is; and a determination result output unit that outputs a determination result.

22. The drug recognizing apparatus according to claim 21, wherein the drug determination unit selects a candidate of the drug indicated by the captured image on the basis of the collation result between the captured image and the master image, and wherein the determination result output unit outputs information indicating the selected candidate.

23. The drug recognizing apparatus according to claim 21, further comprising an associated information input unit for inputting associated information relating to the drug indicated by the captured image, wherein the drug determination unit performs the determination with reference to the associated information.

24. The drug recognizing apparatus according to claim 23, wherein the associated information is information on a drug included in prescription data, and wherein the drug determination unit acquires the master image for the drug included in the prescription data from the storage unit, collates the captured image with the acquired master image, and determines whether the drug indicated by the captured image is identical to the drug indicated by the acquired master image.

25. A drug recognizing method that uses an illumination unit that illuminates a drug, an imaging unit that images the drug illuminated by the illumination unit, and a storage unit that stores a master image showing the drug for each drug type, the method comprising:

a step of acquiring a position of the drug on the basis of a captured image obtained by the imaging unit;

a step of determining whether to update the master image on the basis of the acquired position of the drug; and a step of registering a drug area in the captured image as the master image in the storage unit in a case where it is determined that the master image is to be updated, wherein, in the registering step, drug position information indicating the position of the drug is stored in association with the master image in the storage unit, and wherein, in the determining step, whether to update the master image on the basis of the position of the drug imaged by the imaging unit and the drug position information associated with the master image is determined.

26. A non-transitory, computer-readable recording medium on which a program causing a computer to execute the drug recognizing method according to claim 25 is recorded.

* * * * *